US011576634B2

(12) United States Patent
Bouhnik et al.

(10) Patent No.: US 11,576,634 B2
(45) Date of Patent: Feb. 14, 2023

(54) SYSTEMS AND METHODS FOR CONTROLLING MOTION OF DETECTORS HAVING MOVING DETECTOR HEADS

(71) Applicant: GE Precision Healthcare LLC, Wauwatosa, WI (US)

(72) Inventors: Jean-Paul Bouhnik, Zichon Yaacov (IL); Tzachi Rafaeli, Tirat Carmel (IL); Gil Kovalski, Tirat Carmel (IL); Yariv Grobshtein, Haifa (IL); Riyad Mahameed, Umm al-Fahm (IL); Yaron Hefetz, Kubbutz Alonim (IL); Einat Binyamin, Giv'at-Ada (IL); Yulim Zingerman, Netanya (IL); Nurit Rivka Wartski, Tirat Carmel (IL)

(73) Assignee: GE Precision Healthcare LLC, Wauwatosa, WI (US)

( * ) Notice: Subject to any disclaimer, the term of this patent is extended or adjusted under 35 U.S.C. 154(b) by 858 days.

(21) Appl. No.: 16/370,188

(22) Filed: Mar. 29, 2019

(65) Prior Publication Data

US 2019/0223816 A1 Jul. 25, 2019

Related U.S. Application Data

(63) Continuation of application No. 14/140,052, filed on Dec. 24, 2013, now Pat. No. 10,492,745, which is a (Continued)

(51) Int. Cl.
*A61B 6/00* (2006.01)
*A61B 6/03* (2006.01)
(Continued)

(52) U.S. Cl.
CPC ............ *A61B 6/4266* (2013.01); *A61B 6/037* (2013.01); *A61B 6/06* (2013.01); *A61B 6/4258* (2013.01);
(Continued)

(58) Field of Classification Search
CPC ............................ A61B 6/4266; A61B 6/4258
See application file for complete search history.

(56) References Cited

U.S. PATENT DOCUMENTS 5,847,398 A * 12/1998 Shahar .................. G01T 1/243
250/370.09
6,140,650 A 10/2000 Berlad
(Continued)

FOREIGN PATENT DOCUMENTS

WO 2008135994 A2 11/2008

OTHER PUBLICATIONS

Meikle et al., "Accelerated EM reconstruction in total-body PET: potential for improving tumour detectability," 1994, Physics in Medicine and Biology, vol. 39, pp. 1689-1704.
(Continued)

*Primary Examiner* — Joseph M Santos Rodriguez
(74) *Attorney, Agent, or Firm* — The Small Patent Law Group LLC; Dean D. Small

(57) ABSTRACT

An imaging system is provided that includes a gantry, at least five detector units mounted to the gantry, a corresponding collimator for each of the detector units, at least one processing unit, and a controller. Each collimator has septa defining plural bores for each pixel of at least some of a plurality of pixels of the detector unit. A corresponding interior septum of the collimator is disposed above an internal portion of a corresponding pixel of the at least some of the plurality of pixels. The at least one processing unit is configured to obtain object information corresponding to the object to be imaged. The controller is configured to control an independent rotational movement of each the detector units used to acquire scanning information by detecting emissions from the object, wherein the controller rotates each of the detector units at a corresponding sweep rate.

17 Claims, 27 Drawing Sheets

Related U.S. Application Data continuation-in-part of application No. 14/040,108, filed on Sep. 27, 2013, now Pat. No. 10,575,802.

(51) Int. Cl.
  *A61B 6/06* (2006.01)
  *A61B 6/04* (2006.01)
(52) U.S. Cl.
  CPC ............. *A61B 6/54* (2013.01); *A61B 6/544* (2013.01); *A61B 6/545* (2013.01); *A61B 6/0407* (2013.01)

(56) References Cited

U.S. PATENT DOCUMENTS

| | | |
|---|---|---|
| 6,201,247 B1 | 3/2001 | Lutheran et al. |
| 6,239,438 B1 | 5/2001 | Schubert |
| 6,647,283 B2 | 11/2003 | Klotz |
| 6,748,044 B2 | 6/2004 | Sabol et al. |
| 6,943,355 B2 | 9/2005 | Schwartz et al. |
| 7,026,623 B2 | 4/2006 | Oaknin et al. |
| 7,381,959 B2 | 6/2008 | Manjeshwar et al. |
| 7,671,331 B2 | 3/2010 | Hefetz et al. |
| 8,280,124 B2 | 10/2012 | Dichterman et al. |
| 2002/0191828 A1 | 12/2002 | Colbeth et al. |
| 2005/0145797 A1 | 7/2005 | Oaknin et al. |
| 2006/0108532 A1 | 5/2006 | Ohana et al. |
| 2007/0018108 A1 | 1/2007 | Kitamura |
| 2008/0029704 A1* | 2/2008 | Hefetz ............... A61B 6/4266 250/363.01 |
| 2012/0108948 A1* | 5/2012 | Jansen ............... G21K 1/025 250/515.1 |
| 2013/0168567 A1 | 7/2013 | Wartski et al. |

OTHER PUBLICATIONS

Park et al., "Performance of a high-sensitivity dedicated cardiac SPECT scanner for striatal uptake quantification in the brain based on analysis of projection data," Med. Phys. 40 (4), Apr. 2013.

Riddell et al., "Noise reduction in oncology FOG PET images by iterative reconstruction: a quantitative assessment," 2001, the Journal of Nuclear Medicine, vol. 42, No. 9, pp. 1316-1323.

Shepp et al., "Maximum likelihood reconstruction for emission tomography," 1982, IEEE Transaction on Medical Imaging, vol. MJ-1, No. 2, pp. 113-121.

PCT Search Report and Written Opinion issued in connection with corresponding Application No. PCT/IL2014/050848 dated Feb. 5, 2015.

* cited by examiner

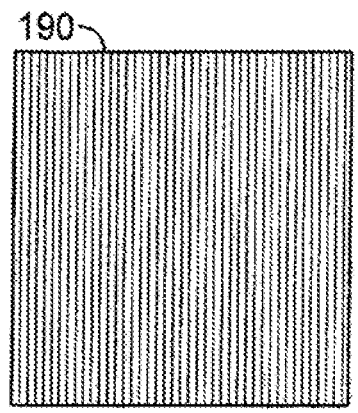 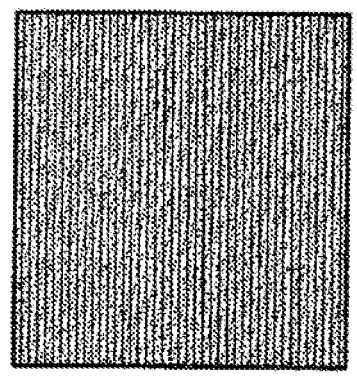
(a) (b)
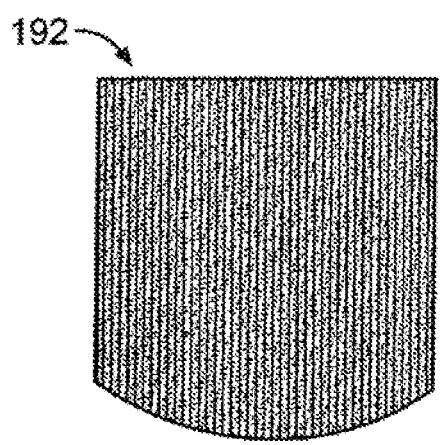 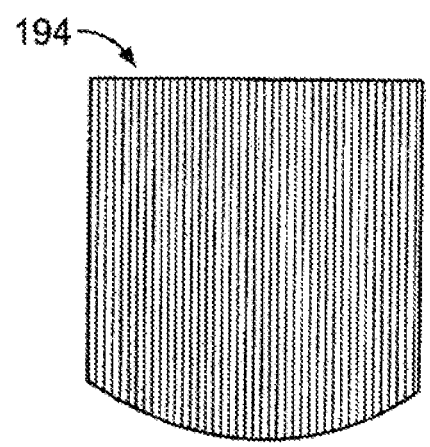
(c) (d)
FIG. 7

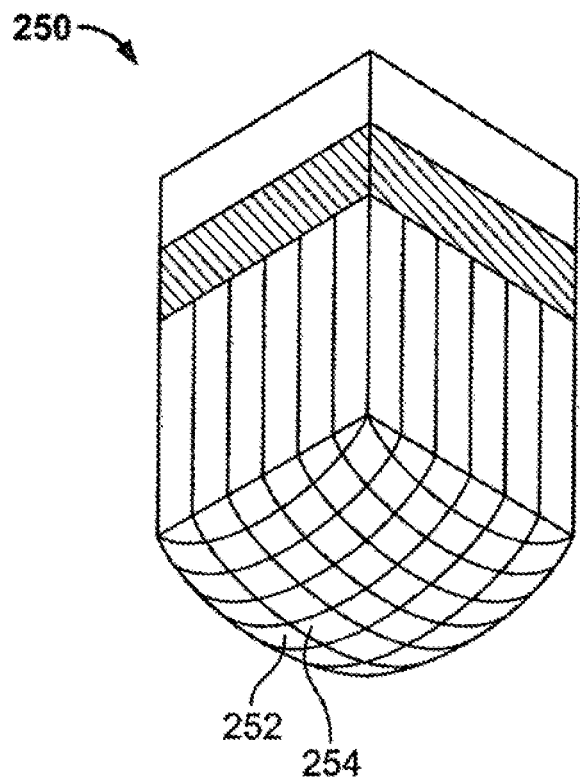
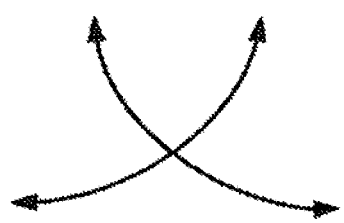
FIG. 12

SYSTEMS AND METHODS FOR CONTROLLING MOTION OF DETECTORS HAVING MOVING DETECTOR HEADS

RELATED APPLICATIONS

The present application is a continuation application of U.S. patent application Ser. No. 14/140,052, entitled "SYSTEMS AND METHODS FOR CONTROLLING MOTION OF DETECTORS HAVING MOVING DETECTOR HEADS," (the 052 Application) filed Dec. 24, 2013, the content of which is incorporated herein by reference in its entirety. The 052 application is a continuation-in-part application of U.S. patent application Ser. No. 14/040,108, entitled "SYSTEMS AND METHODS FOR CONTROLLING MOTION OF DETECTORS HAVING MOVING DETECTOR HEADS," filed Sep. 27, 2013, the content of which is incorporated herein by reference in its entirety.

BACKGROUND OF THE INVENTION

The subject matter disclosed herein relates generally to apparatus and methods for diagnostic medical imaging, such as Nuclear Medicine (NM) imaging.

In NM imaging, systems with multiple detectors or detector heads may be used to image a subject, such as to scan a region of interest. For example, the detectors may be positioned adjacent the subject to acquire NM data, which is used to generate a three-dimensional (3D) image of the subject.

Single Photon Emission Computed Tomography (SPECT) systems may have moving detector heads, such as gamma detectors positioned to focus on a region of interest. For example, a number of gamma cameras may be moved (e.g., rotated) to different angular positions for acquiring image data. The acquired image data is then used to generate the 3D images.

Resolution of gamma detectors is a convolution of the detector resolution (mainly pixel size) and the collimator resolution. Collimator resolution degrades with the distance of the collimator from the subject. In conventional SPECT camera systems with multiple swinging detector heads, the detectors swing about a fixed pivot (usually inside a protective case). As a result of the configuration of these systems, including the detectors and collimators, the gamma cameras often have to be placed at an additional distance from the subject. This increase in distance results in a degrading of resolution.

Thus, known systems have degradation in imaging resolution as a result of the limits to which the gamma cameras can move in proximity to the subject because of the configuration of the detector head or collimator used, and/or the types of control of movement of the gamma cameras. Further, known systems may expose patients to levels of radiation that is higher than necessary.

BRIEF DESCRIPTION OF THE INVENTION

In one embodiment, an imaging system is provided that includes a gantry, a detector unit mounted to the gantry, at least one processing unit, and a controller. The at least one processing unit is configured to obtain object information corresponding to an object to be imaged, and to automatically determine, based on the object information, at least one first portion of the object and at least one second portion of the object. The controller is configured to control a rotational movement of the detector unit. The detector unit is rotatable at a sweep rate from a first position to a second position defining a range of view of the object to be imaged, and the controller is configured to rotate the detector unit from the first position to the second position at an uneven sweep rate. The uneven sweep rate varies during the rotation from the first position to the second position, wherein a larger amount of scanning information is obtained for the at least one first portion than for the at least one second portion.

In another embodiment, an imaging system is provided that includes a gantry, a plurality of detector units, at least one processing unit, and a controller. The plurality of detector units are mounted to the gantry, and are individually movable including translational movement and rotational movement. The least one processing unit is configured to obtain object information corresponding to an object to be imaged, and to automatically determine, based on the object information, at least one first portion of the object and at least one second portion of the object. The controller is configured to control the rotational movement of the plurality of detector units. The detector units are individually rotatable from corresponding first positions to second positions defining a range of view of an object to be imaged, and the controller is configured to rotate at least one detector unit from the first position of the detector unit to the second position of the detector unit at an uneven sweep rate. The uneven sweep rate is configured to vary during the rotation from the first position to the second position, wherein a larger amount of scanning information is obtained for the at least one first portion than for the at least one second portion.

In another embodiment, a method for imaging an object is provided. The method includes obtaining object information corresponding to an object to be imaged. The method also includes determining, based on the object information, at least one first portion of the object and at least one second portion of the object. The method further includes rotating at least one detector unit at a sweep rate from a first position to a second position defining a range of view of the object to be imaged to acquire the scanning information. Rotating the detector unit includes varying the sweep rate during the rotation from the first position to the second position. The sweep is varied such that a larger amount of scanning information is obtained for the at least one first portion than for the at least one second portion.

BRIEF DESCRIPTION OF THE DRAWINGS

FIG. 7 is a diagram illustrating the manufacture of a collimator in accordance with an embodiment.

FIG. 12 is a diagram illustrating a collimator arrangement in accordance with another embodiment.

DETAILED DESCRIPTION OF THE INVENTION

Figure 1:
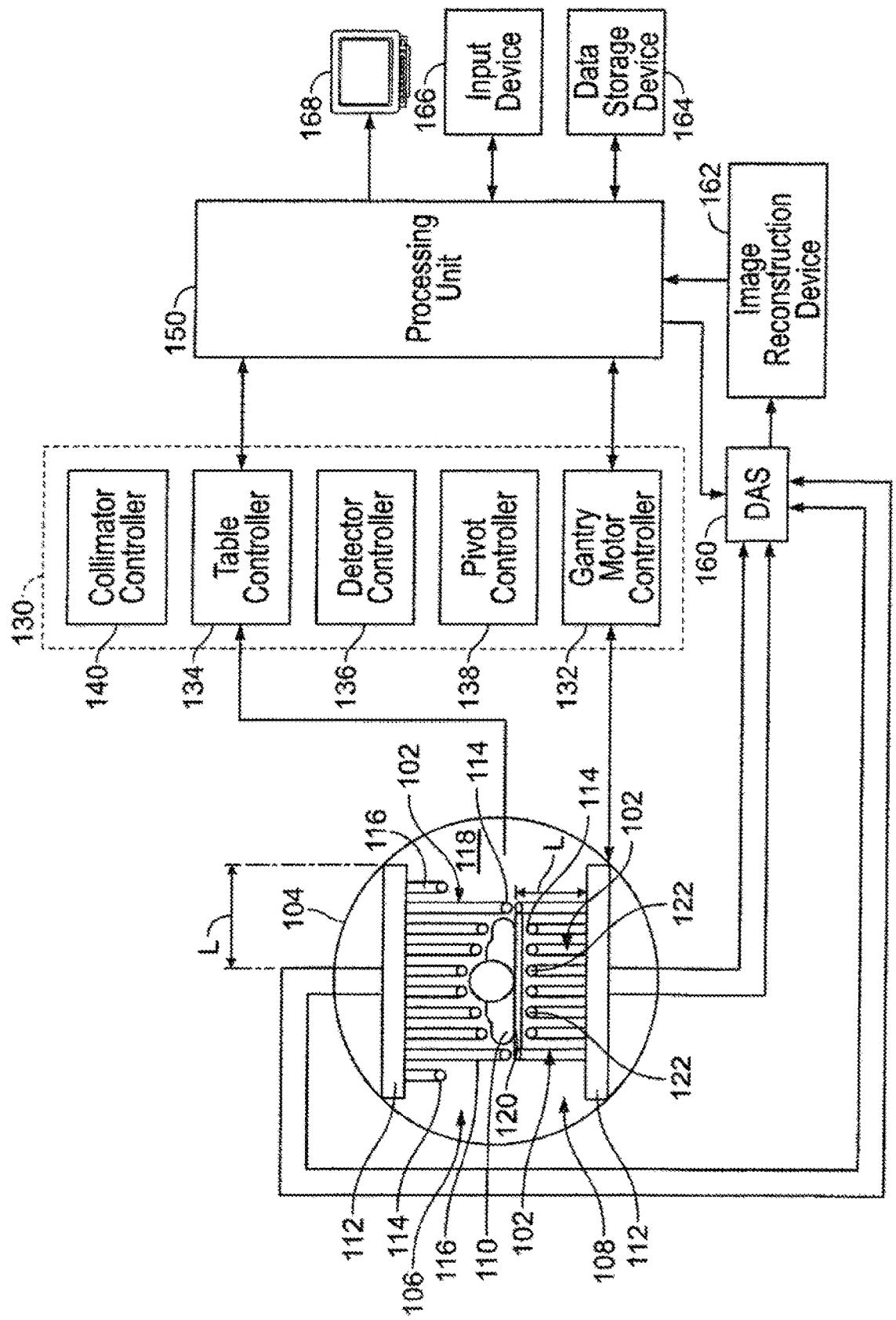
FIG. 1 is a schematic block diagram of a Nuclear Medicine (NM) imaging system in accordance with an embodiment.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and preceded with the word "a" or "an" should be understood as not excluding plural of said elements or steps, unless such exclusion is explicitly stated. Furthermore, references to "one embodiment" of are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide systems and methods for controlling the movement of a plurality of imaging detectors to position the imaging detectors to acquire image data. For example, in various embodiments, an imaging system having one or more Nuclear Medicine (NM) cameras having an array of heads that are individually and independently movable is provided. In some embodiments, one or more of the heads are capable of a plurality of types of movement, such as translation, rotation, pivoting, and/or swiveling. The NM cameras in various embodiments are configured to acquire Single Photon Emission Computed Tomography (SPECT) data, such as when moving the detector heads. For example, various embodiments provide combination movements or complex motion of the detectors, such as a combination of up/down movement with swinging motion. In some embodiments, the motion may include, for example, side-to-side motion.

In some embodiments, the imaging detectors may be controlled to provide a varying angular velocity or otherwise varying sweep rate during rotation of the detectors. The sweep may be a focused acquisition, with more scanning time (and information acquisition) performed for volumes corresponding to a view of interest and/or organ(s) of interest. More time may be spent in a center of a view than in a peripheral area of a view. Additional acquisition steps or additional angular sampling may be provided for a region of interest than for other regions. In some embodiments, information may be acquired while a gantry rotates. Additionally or alternatively, detectors may rotate or sweep independently of gantry rotation. A first sweep may be a full range sweep and used to obtain an initial or scout image from which a region of interest or organ of interest may be determined. Movement of the detectors and/or gantry may be continuous, or performed in a "step-and shoot" manner.

In some embodiments, data may be acquired while a gantry rotates, but individual detectors do not sweep or pivot independently of the gantry, with collimators of the detectors oriented toward the center of the gantry and/or the center of a region of interest. Such imaging may be used to improve image quality at a center of a field of view.

It may be noted that in SPECT cameras using multiple detector heads that pivot or swing, the time to obtain a clinically useful image depends on the size of the scanned organ. Generally, an imaged volume of interest extends over a longitudinal range corresponding to the width of scanning heads, and is limited to the body width in a transverse direction, or to an organ of interest. During a whole body SPECT, a patient may be moved with respect to the camera and a 3D image of a large section or the entire body is obtained. In various embodiments, the position, range of rotation, and control of the sweep or rotation rate of the detectors is controlled according to the portion of the body currently being scanned, for example to allow increased scanning of portions for which more information is required to provide a clinically useful image, and reduced scanning of portions for which less information is required.

Additionally, imaging detectors or camera heads are coupled with collimators in various embodiments. In some embodiments, collimators are provided that have uneven bores, in particular, bores having different lengths. For example, instead of having collimators that are "box like" shaped with all bores having the same length, different length bores (e.g., uneven lengths) may be provided. In some embodiments, the varying collimator bore length increases resolution at the central or middle section of the detector and reduced or eliminates a gap between adjacent detectors.

Various embodiments provide improved imaging. For example, acquisition time may be reduced. As another example, resolution or image quality may be increased for regions or interest or organs of interest. As one more example, detector unit size may be decreased, allowing for closer or more precise placement and/or increased numbers of detectors that may be placed near an object to be imaged.

FIG. 1 is a schematic illustration of a NM imaging system 100 having a plurality of imaging detectors mounted on a gantry (which may be mounted, for example, in rows, in an iris shape, or other configurations). In particular, a plurality of imaging detectors 102 are mounted to a gantry 104. In the illustrated embodiment, the imaging detectors 102 are configured as two separate detector arrays 106 and 108 coupled to the gantry 104 above and below a subject 110 (e.g., a patient), as viewed in FIG. 1. The detector arrays 106 and 108 may be coupled directly to the gantry 104, or may be coupled via support members 112 to the gantry 104 to allow movement of the entire arrays 106 and/or 108 relative to the gantry 104 (e.g., translating movement in the left or right direction as viewed in FIG. 1). Additionally, each of the imaging detectors 102 includes a detector unit 114, at least some of which are mounted to a movable detector carrier 116 (e.g., a support arm or actuator that may be driven by a motor to cause movement thereof) that extends from the gantry 104. In some embodiments, the detector carriers 116 allow movement of the detector units 114 towards and away from the subject 110, such as linearly. Thus, in the illustrated embodiment the detector arrays 106 and 108 are mounted in parallel above and below the subject 110 and allow linear movement of the detector units 114 in one direction (indicated by the arrow L), illustrated as perpendicular to the support member 112 (that are coupled generally horizontally on the gantry 104). However, other configurations and orientations are possible as described herein. It should be noted that the movable detector carrier 116 may be any type of support that allows movement of the detector units 114 relative to the support member 112 and/or gantry 104, which in various embodiments allows the detector units 114 to move linearly towards and away from the support member 112.

Each of the imaging detectors 102 in various embodiments are smaller than a conventional whole body or general purpose imaging detector. A conventional imaging detector may be large enough to image most or all of a width of a patient's body at one time and may have a diameter or a larger dimension of approximately 50 cm or more. In contrast, each of the imaging detectors 102 may include one or more detector units 114 coupled to a respective detector carrier 116 and having dimensions of 4 cm to 20 cm and may be formed of Cadmium Zinc Telluride (CZT) tiles or modules. For example, each of the detector units 114 may be 8×8 cm in size and be composed of a plurality of CZT pixelated modules (not shown). For example, each module may be 4×4 cm in size and have 16×16=256 pixels. In some embodiments, each detector unit 114 includes a plurality of modules, such as an array of 1×7 modules. However, different configurations and array sizes are contemplated including, for example, detector units 114 having multiple rows of modules.

It should be understood that the imaging detectors 102 may be different sizes and/or shapes with respect to each other, such as square, rectangular, circular or other shape. An actual field of view (FOV) of each of the imaging detectors 102 may be directly proportional to the size and shape of the respective imaging detector.

The gantry 104 may be formed with an aperture 118 (e.g., opening or bore) therethrough as illustrated. A patient table 120, such as a patient bed, is configured with a support mechanism (not shown) to support and carry the subject 110 in one or more of a plurality of viewing positions within the aperture 118 and relative to the imaging detectors 102. Alternatively, the gantry 104 may comprise a plurality of gantry segments (not shown), each of which may independently move a support member 112 or one or more of the imaging detectors 102.

The gantry 104 may also be configured in other shapes, such as a "C", "H" and "L", for example, and may be rotatable about the subject 110. For example, the gantry 104 may be formed as a closed ring or circle, or as an open arc or arch which allows the subject 110 to be easily accessed while imaging and facilitates loading and unloading of the subject 110, as well as reducing claustrophobia in some subjects 110.

Additional imaging detectors (not shown) may be positioned to form rows of detector arrays or an arc or ring around the subject 110. By positioning multiple imaging detectors 102 at multiple positions with respect to the subject 110, such as along an imaging axis (e.g., head to toe direction of the subject 110) image data specific for a larger FOV may be acquired more quickly.

Each of the imaging detectors 102 has a radiation detection face, which is directed towards the subject 110 or a region of interest within the subject. The radiation detection faces are each covered by or have coupled thereto a collimator 122. The actual FOV for each of the imaging detectors 102 may be increased, decreased, or relatively unchanged by the type of collimator 122. As described in more detail herein, in some embodiments, the collimator 122 includes at least some collimator bores having different axial lengths.

In one embodiment, the collimator 122 is a multi-bore collimator, such as a parallel hole collimator. However, other types of collimators, such as converging or diverging collimators may optionally or alternatively be used. Other examples for the collimator 122 include pinhole, parallel-beam converging, diverging fan-beam, converging or diverging cone-beam, multi-bore converging, multi-bore converging fan-beam, multi-bore converging cone-beam, multi-bore diverging, or other types of collimator.

Optionally, multi-bore collimators may be constructed to be registered with pixels of the detector units 114, which in one embodiment are CZT detectors. However, other materials may be used. Registered collimation may improve spatial resolution by forcing photons going through one bore to be collected primarily by one pixel. Additionally, registered collimation may improve sensitivity and energy response of pixelated detectors as detector area near the edges of a pixel or inbetween two adjacent pixels may have reduced sensitivity or decreased energy resolution or other performance degradation. Having collimator septa directly above the edges of pixels reduces the chance of a photon impinging at these degraded-performance locations, without decreasing the overall probability of a photon passing through the collimator.

A controller unit 130 may control the movement and positioning of the patient table 120, imaging detectors 102 (which may be configured as one or more arms), gantry 104 and/or the collimators 122 (that move with the imaging detectors 102 in various embodiments, being coupled thereto). A range of motion before or during an acquisition, or between different image acquisitions, is set to maintain the actual FOV of each of the imaging detectors 102 directed, for example, towards or "aimed at" a particular area or region of the subject 110 or along the entire subject 110. The motion may be a combined or complex motion in multiple directions simultaneously, concurrently, or sequentially as described in more detail herein.

The controller unit 130 may have a gantry motor controller 132, table controller 134, detector controller 136, pivot controller 138, and collimator controller 140. The controllers 130, 132, 134, 136, 138, 140 may be automatically commanded by a processing unit 150, manually controlled by an operator, or a combination thereof. The gantry motor controller 132 may move the imaging detectors 102 with respect to the subject 110, for example, individually, in segments or subsets, or simultaneously in a fixed relationship to one another. For example, in some embodiments, the gantry controller 132 may cause the imaging detectors 102 and/or support members 112 to move relative to or rotate about the subject 110, which may include motion of less than or up to 180 degrees (or more).

The table controller 134 may move the patient table 120 to position the subject 110 relative to the imaging detectors 102. The patient table 120 may be moved in up-down directions, in-out directions, and right-left directions, for example. The detector controller 136 may control movement of each of the imaging detectors 102 to move together as a group or individually as described in more detail herein. The detector controller 136 also may control movement of the imaging detectors 102 in some embodiments to move closer to and farther from a surface of the subject 110, such as by controlling translating movement of the detector carriers 116 linearly towards or away from the subject 110 (e.g., sliding or telescoping movement). Optionally, the detector controller 136 may control movement of the detector carriers 116 to allow movement of the detector array 106 or 108. For example, the detector controller 136 may control lateral movement of the detector carriers 116 illustrated by the L arrow (and shown as left and right as viewed in FIG. 1). In various embodiments, the detector controller 136 may control the detector carriers 116 or the support members 112 to move in different lateral directions.

The pivot controller 138 may control pivoting or rotating movement of the detector units 114 at ends of the detector carriers 116 and/or pivoting or rotating movement of the detector carrier 116. For example, one or more of the detector units 114 or detector carriers 116 may be rotated about at least one axis to view the subject 110 from a plurality of angular orientations to acquire, for example, 3D image data in a 3D SPECT or 3D imaging mode of operation. The collimator controller 140 may adjust a position of an adjustable collimator, such as a collimator with adjustable strips (or vanes) or adjustable pinhole(s).

It should be noted that motion of one or more imaging detectors 102 may be in directions other than strictly axially or radially, and motions in several motion directions may be used in various embodiment. Therefore, the term "motion controller" may be used to indicate a collective name for all motion controllers. It should be noted that the various controllers may be combined, for example, the detector controller 136 and pivot controller 138 may be combined to provide the different movements described herein.

Prior to acquiring an image of the subject 110 or a portion of the subject 110, the imaging detectors 102, gantry 104, patient table 120 and/or collimators 122 may be adjusted as discussed in more detail herein, such as to first or initial imaging positions, as well as subsequent imaging positions. The imaging detectors 102 may each be positioned to image a portion of the subject 110. Alternatively, one or more of the imaging detectors 102 may not be used to acquire data, such as the imaging detectors 102 at ends of the detector arrays 106 and 108, which as illustrated in FIG. 1 are in a retracted position away from the subject 110. Positioning may be accomplished manually by the operator and/or automatically, which may include using, for example, image information such as other images acquired before the current acquisition, such as by another imaging modality such as X-ray Computed Tomography (CT), MM, X-Ray, PET or ultrasound. In some embodiments, the additional information for positioning, such as the other images, may be acquired by the same system, such as in a hybrid system (e.g., a SPECT/CT system). Additionally, the detector units 114 may be configured to acquire non-NM data, such as x-ray CT data. In some embodiments, a multi-modality imaging system may be provided, for example, to allow performing NM or SPECT imaging, as well as x-ray CT imaging, which may include a dual-modality or gantry design as described in more detail herein.

After the imaging detectors 102, gantry 104, patient table 120, and/or collimators 122 are positioned, one or more images, such as three-dimensional (3D) SPECT images are acquired using one or more of the imaging detectors 102, which may include using a combined motion that reduces or minimizes spacing between detector units 114. The image data acquired by each imaging detector 102 may be combined and reconstructed into a composite image or 3D images in various embodiments.

In one embodiment, at least one of detector arrays 106 and/or 108, gantry 104, patient table 120, and/or collimators 122 are moved after being initially positioned, which includes individual movement of one or more of the detector units 114 (e.g., combined lateral and pivoting movement). For example, at least one of detector arrays 106 and/or 108 may be moved laterally while pivoted. Thus, in various embodiments, a plurality of small sized detectors, such as the detector units 114 may be used for 3D imaging, such as when moving or sweeping the detector units 114 in combination with other movements.

In various embodiments, a data acquisition system (DAS) 160 receives electrical signal data produced by the imaging detectors 102 and converts this data into digital signals for subsequent processing. However, in various embodiments, digital signals are generated by the imaging detectors 102. An image reconstruction device 162 (which may be a processing device or computer) and a data storage device 164 may be provided in addition to the processing unit 150. It should be noted that one or more functions related to one or more of data acquisition, motion control, data processing and image reconstruction may be accomplished through hardware, software and/or by shared processing resources, which may be located within or near the imaging system 100, or may be located remotely. Additionally, a user input device 166 may be provided to receive user inputs (e.g., control commands), as well as a display 168 for displaying images.

Figure 2:
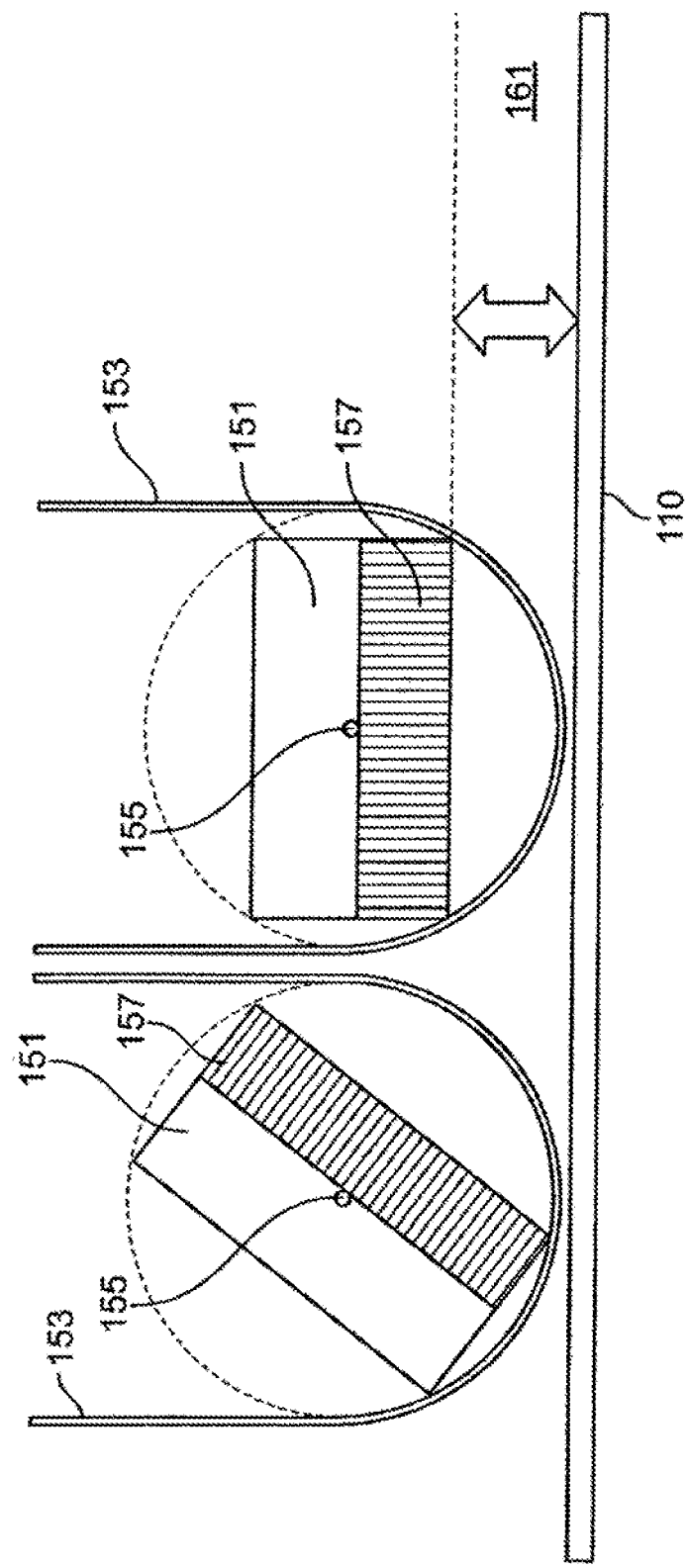
FIG. 2 is a diagram illustrating detectors having movement about one axis.

FIG. 2 schematically demonstrates a detector 151 within a housing 153 having only a single rotating or pivoting point. In this configuration, when the detector 151 (e.g., a CZT detector) is equipped with a flat collimator 157 (e.g., collimator having a planar face) is to rotate about a fixed pivot point 155, in order to avoid collision with a subject 110 (illustrated as a substantially flat patient), an unavoidable gap 161 is created between the face of the collimator 157 and the subject 110.

Figure 3:
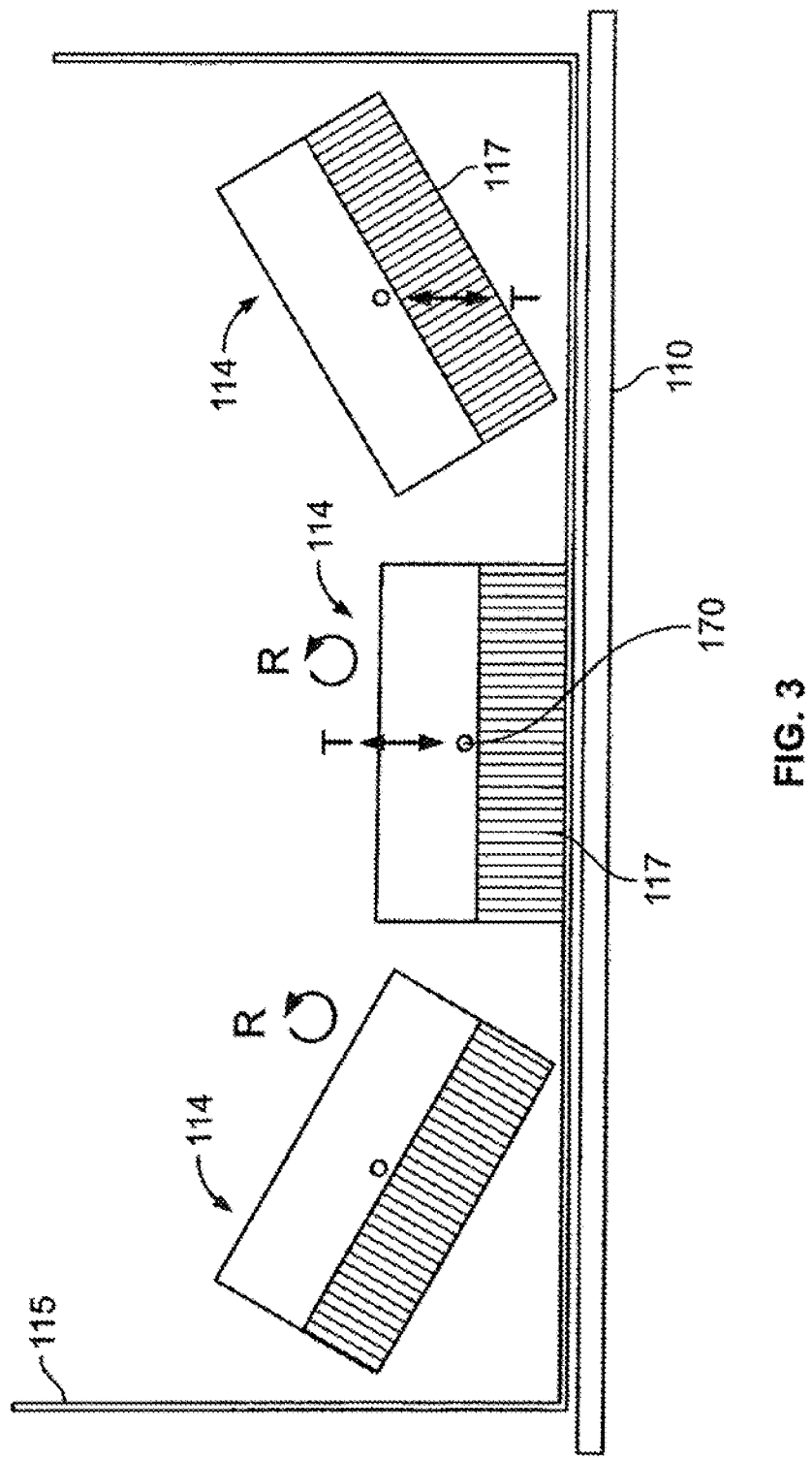
FIG. 3 is a diagram illustrating uncovered detectors in accordance with various embodiments.

In operation, and as shown, for example, in FIG. 3, a combined motion of the detector units 114 is used to position the detector units 114 or move the detector units 114 before, during, and/or after imaging. FIG. 3 schematically depicts a plurality of detector units 114, all within one patient-protecting cover 115. The coordinated rotational (or pivoting) and up/down motion seen in FIG. 3 are performed by each of the detector units 114 to reduce or minimize the distance from the face of the collimator 117 and the subject 110. The optional cover 115 may be removed, for example, when the detector units 114 are placed below the patient table 120

More particularly, as shown in FIG. 3, one or more of the detector units 114 may be positioned or repositioned using a combination of movements that are performed is some embodiments concurrently. It should be noted that the movements of different detector units 114 likewise may be performed simultaneously, concurrently, or sequentially. As illustrated in FIG. 3, one type of combined movement includes rotational movement (illustrated by the R arrow, which may be or include pivoting movement in some embodiments) and linear or translation movement (illustrated by the T arrow). It should be noted that while the translation movement is illustrated as up and down in FIG. 2, translation movement in other transverse or perpendicular directions may be provided, such as left and right.

Additionally, the rotating movement may be provided about different rotating axes or points, such as about a rod or at a pivot point. In FIG. 2, the rotation is about an axis 170, which may be a rotation or pivot point. For example, depending on the orientation of the axis 170, the detector units 114 may rotate in different directions.

Figure 4:
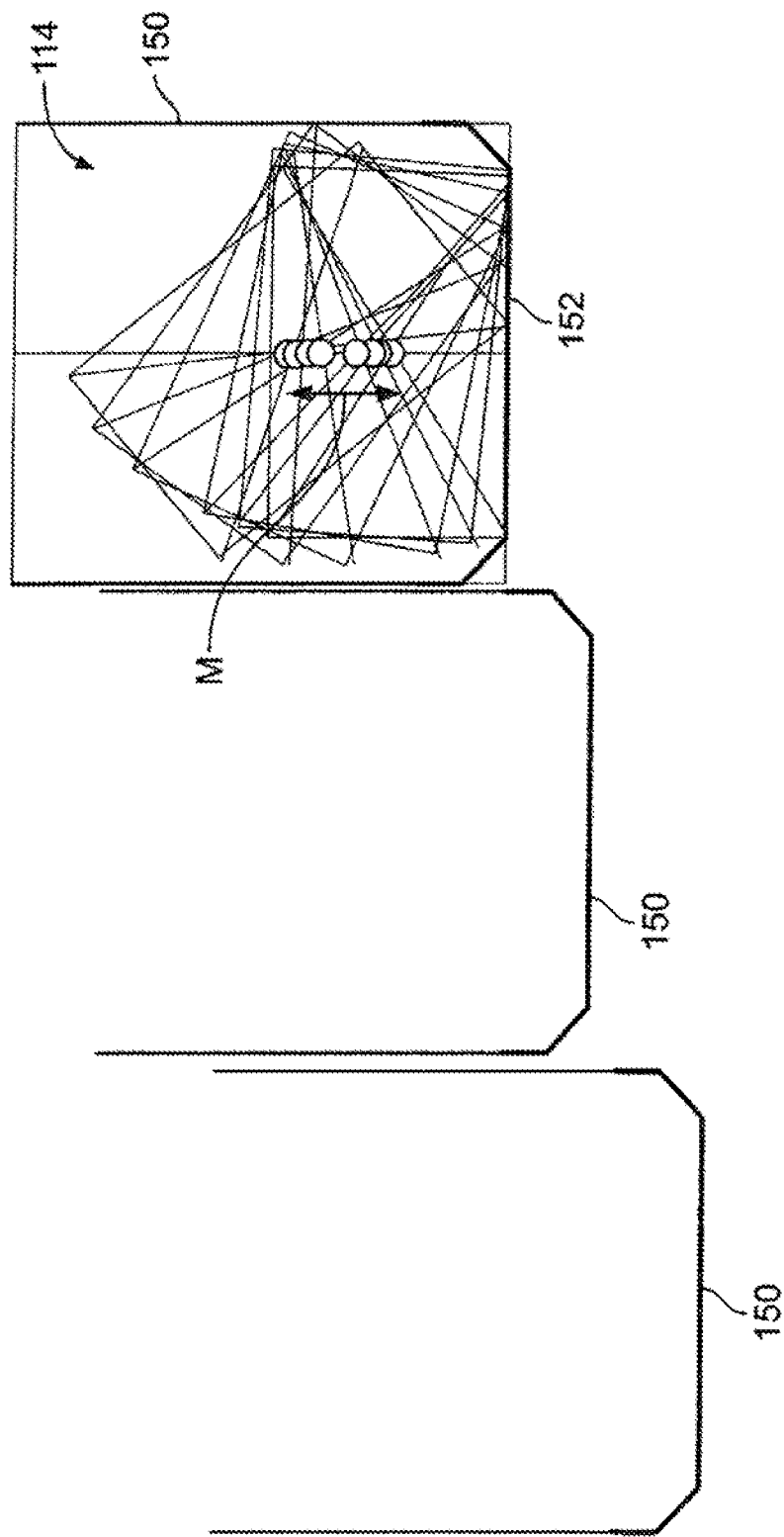
FIG. 4 is a diagram illustrating detector movement in accordance with various embodiments.

It should be noted that depending on the state of movement of the detector units 114 and the position thereof, a distance D exists between the detector units 114 and the front face 174 of the housing (not shown) of the detector units 114. For example, as illustrated in FIG. 4, a plurality of detector units 114 each having a respective housing 150 may be provided. As can be seen, a range of motion (illustrated by the M arrow) within the housing may be provided (up and down as seen in FIG. 4) in addition to rotational movement (and may be defined or set based on the object to be scanned). The rightmost detector unit 114 in FIG. 4 shows a movement pattern in accordance with one embodiment that allows the housings 150 to be positioned adjacent each other with reduced or minimal distance therebetween. As can be seen, by translating and rotating the detector units 114, the angle of the detector units 114 may be changed to focus the detector units 114 at different views, while maintaining a small footprint for the housing 150. In some embodiments, no housings 150 are provided.

It should be noted that the various movements of the detector units 114 may be provided using any suitable drive and control means, such as using one or more motors. Additionally or optionally, a proximity sensor 152 or other patient safety device may be used to detect contact or impending contact with a patient. The proximity sensor 152 may be provided in some embodiments as known in the art.

Figure 5:
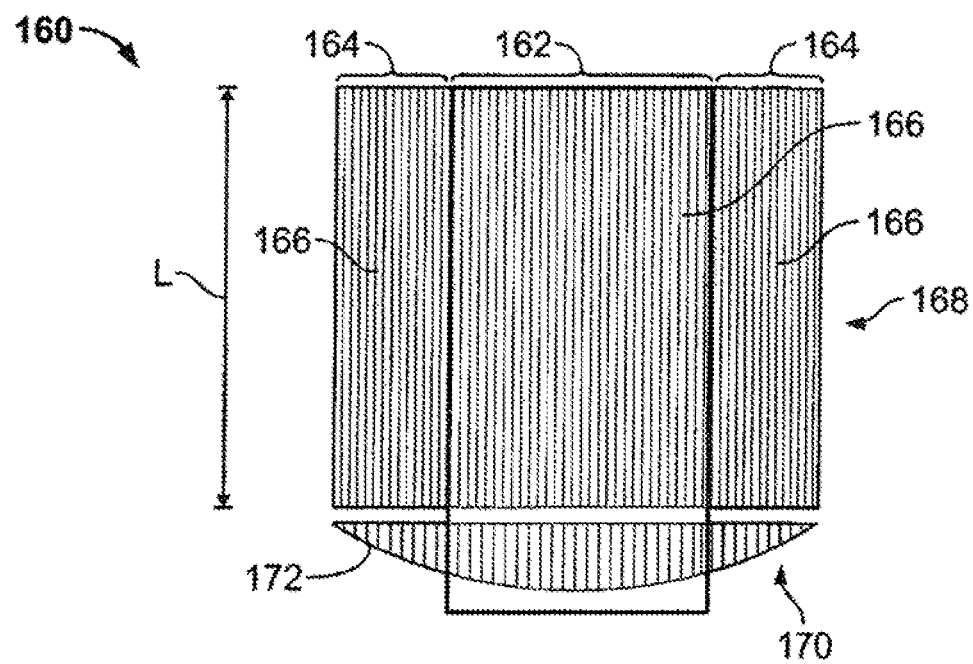
FIG. 5 is a diagram illustrating a collimator in accordance with an embodiment having a higher resolution area.

In various embodiments, a collimator 160 arrangement may be provided having variable length bores, for example, as illustrated in FIG. 5. In this embodiment, collimator bores 166 in a middle section 162 of the collimator 160 have a greater length (and different lengths) than the collimator bores 166 in side sections 164 of the collimator 160. Accordingly, as a result of the longer bore lengths in the middle section 162, a higher resolution imaging portion or area is defined when compared to the shorter lengths of collimator bores 166 in the side sections 164 (as distance from the object being scanned is related to resolution). In the illustrated embodiment, a top portion 168 and a bottom portion 170 of the collimator are shown as separate merely for ease of explanation and illustration and in various embodiments the collimator bores 166 from top to bottom as seen in FIG. 5 are single channels or pieces.

As can be seen in the illustrated embodiment, the length of the collimator bores 166 decreases from a middle of the middle section 162, through the middle section 162 and to ends of the end sections 164. Thus, in this embodiment, a smoothly curved or arcuate face 172 is formed. It should be noted that the curvature of the face 172 may be varied by changing the amount that the lengths of the collimator bores 166 (such as adjacent collimator bores 166) are different. It should also be noted that some of the collimator bores 166 may have the same length, such as adjacent collimator bores 166 or collimator bores 166 on opposite sides (from left to right) of the collimator 160. Additionally, it should be noted that the face in various embodiments is not limited to be smoothly curved, but may take different configurations, such as other different non-planar configurations (e.g., concave, convex, polygonal, among others).

In some embodiments, the amount of curvature may be varied at only certain portions along the face 172 to change the slope of the curve or different amount of curvature may be provided such as to provide an asymmetric face 172. Additionally, other variations and modifications are contemplated. For example, the length of the collimator bores 166 may be varied differently such as in a stepwise manner such that a smooth face 172 is not provided.

Figure 6:
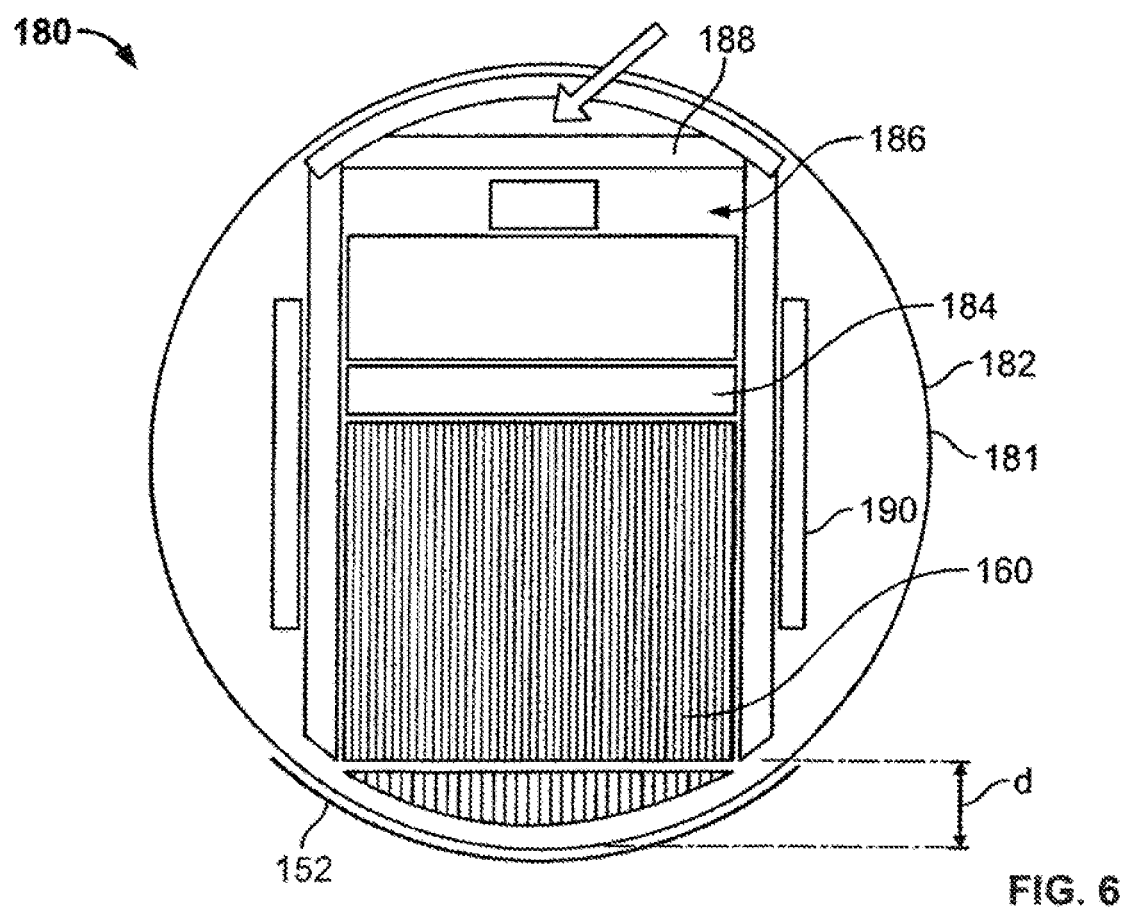
FIG. 6 is a diagram illustrating a collimator arrangement in accordance with an embodiment.

The collimator 170 may be provided as part of the imaging unit 114 to define a variable sensitivity and resolution detector module 180 as shown in FIG. 6. Thus, with the collimator 170, variable sensitivity and resolution may be provided that allows for focused scanning with only a portion of the module 180, for example, performing focused scanning using only image data acquired within the middle section 162. In one embodiment, focused scanning with a partial module may be performed for high resolution brain imaging.

It should be noted that although the housing of the module 180 is illustrated as circular (e.g., circular cross-section) within the circular cross-section region 181 in various embodiments, the housing may have different shapes as desired or needed. Additionally, the location of the components in the module 180 may be varied and different configurations or sizes also may be provided. In the illustrated embodiment, a detector material 184 (such as CZT) is positioned adjacent and behind the collimator 160 as viewed in FIG. 5. In one embodiment, the detector material 184 may have a pixelated structure that is registered with the collimator bores 166 (e.g., one pixel per collimator bore 166). Electronics 186 are coupled to the detector material 184, such as known in the art to read out signals to be processed. Additionally, shielding 188 is provided around the collimator 160, detector material 184, and electronics 186. A holder 190 or other support (e.g., bracket) is provided within the housing, which may take a configuration to maintain the position of the components therein or allow movement as described in more detail herein.

Modifications and variations are contemplated. For example, air cooling may be provided through an aperture (not shown), such as in the shielding 188 on the top of the module 180 as viewed in FIG. 6. It should be noted that the resolution at the central portion of the collimator 172 is further improved as the face of the collimator 172 at a central portion is closer to the subject 110 (as well as having longer bores). For example, the distance seen in FIG. 2 (showing a conventional detector arrangement) is avoided at least for some portion of the face of the collimator and some pivot positions. This increase in resolution may contribute to better image quality.

The collimator 160 may be formed in any suitable manner. In one embodiment, as illustrated in FIG. 7, a plurality of tubes 190 (e.g., lead tubes) are glued together as illustrated at (a). Thereafter, the tubes 190 are filled, for example, with a molten wax at (b). The tubes 190 are then cut at (c) to form a curved face 192 at (c) (e.g., a curved face along one side of the body portion). For example, the tubes 190 may be cut to size or shape with a wire saw or other cutting device. The cutting may be performed to form tubes 190 have different lengths as described in more detail herein. Thereafter the wax is removed at (d) such that the tubes 190 now form different length bores for a collimator 194. Optionally the collimator is attached to a pixelated detector in a registered fashion such that at least some septa between bores are positioned over boundaries between pixels.

Figure 8:
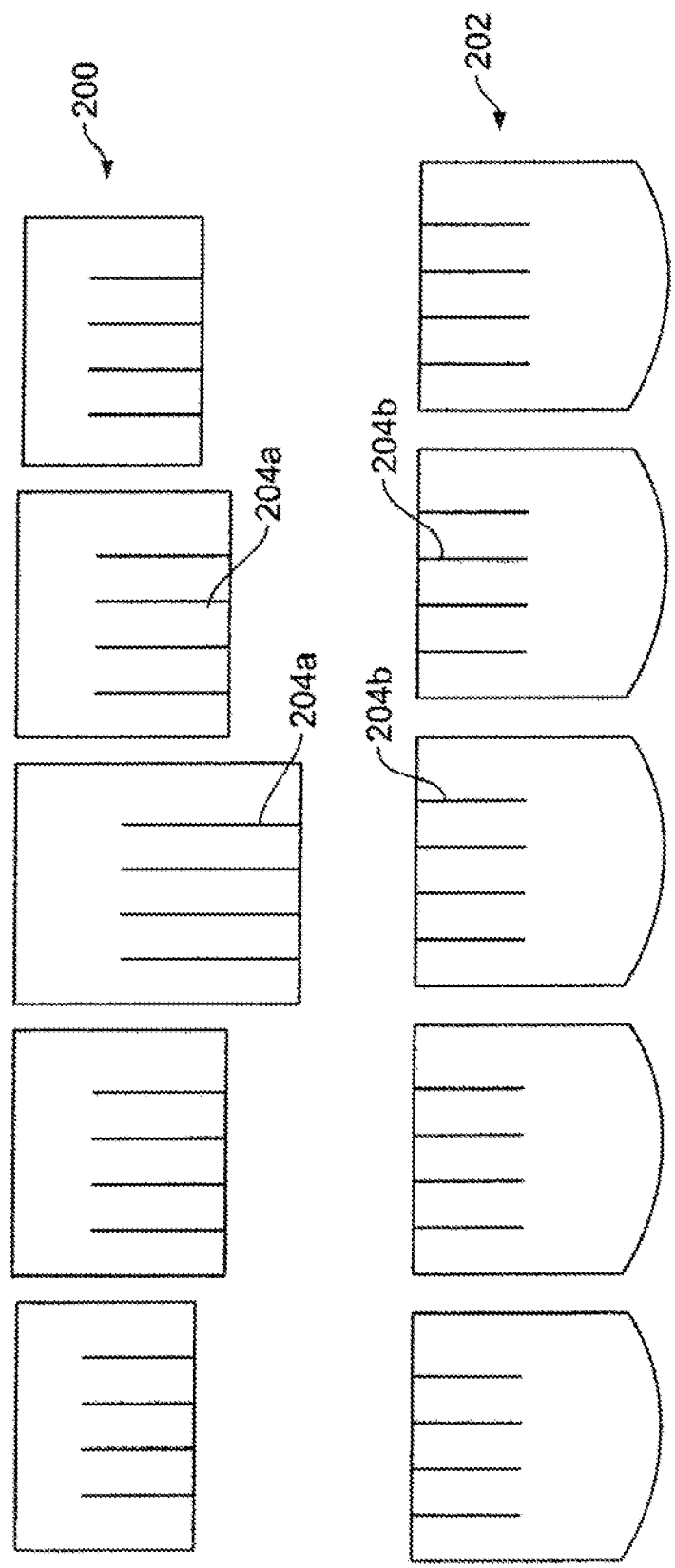
FIG. 8 is a diagram illustrating interlocking sheets for the manufacture of a collimator in accordance with an embodiment.

The manufacturing process may include using a plurality of interlocking sheets, such as the set of sheets 200 or 202 as shown in FIG. 8. For example, the sheets may be sized (e.g., length) and shaped to define a variable bore length collimator as described herein. The set of sheets 200 or 202 may correspond to different sections or portions of the collimator, such that complementary cuts 204*a* and 204*b* are formed to allow interlocking of the sheets 200 or 202 (top and bottom sheets as viewed in FIG. 7).

Figure 9:
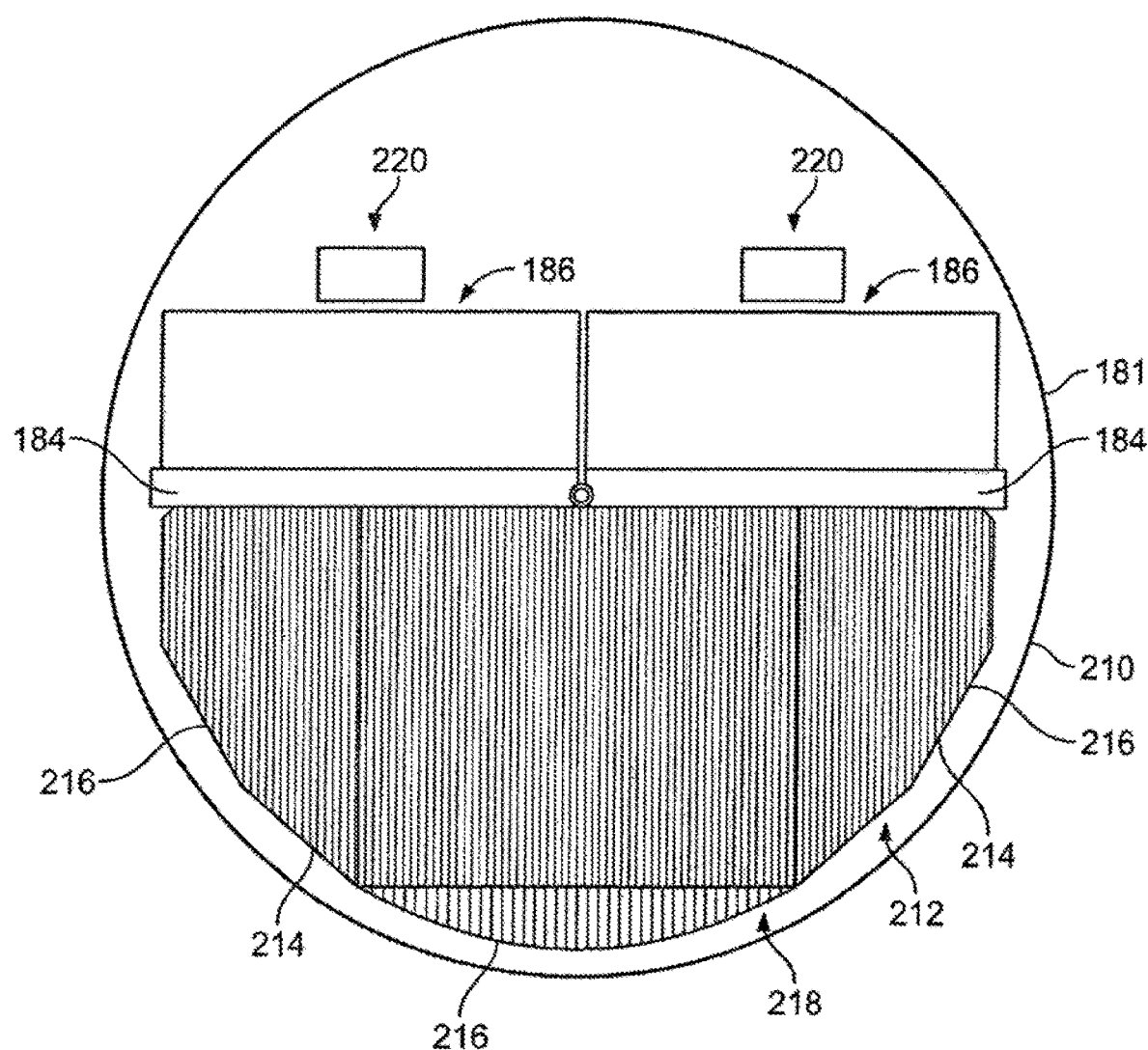
FIG. 9 is a diagram illustrating a collimator arrangement in accordance with another embodiment.

In some embodiments, two modules may be provided per detector head as shown in FIG. 9. However, it should be appreciated that additional modules may be provided (and the two modules shown are for illustration). In particular, within a single housing 210, two sets of CZT material 184 and corresponding electronics 186 may be provided. In this embodiment, a collimator 212 is similarly provided with collimator bores 214 having different lengths. As can be seen, in this embodiment, different sections 216 may be provided that having different curvatures, which may be determined based on the type and amount of movement to be provided within the housing 210. Again, as should be appreciated, the sections 216 are merely shown for ease of description and are not necessarily separate pieces joined together, but may be a single piece. Thus, in this embodiment, the collimator 212 has a curved face 218 that extends across two modules 220 defined by the two sets of CZT material 184 and corresponding electronics 186. It should be appreciated that additional modules 220 may be encompassed by the collimator 212 as desired or needed.

It should be noted that each detector unit may comprise an array of modules, for example 2×2, 2×3, 2×4 modules, etc. Generally, the pixel size of a pixelated NM detector may be selected to be about 1.5 mm to 3 mm, which may be due to physical constrains. In some embodiments, wherein the collimator is a registered collimator, the width of the collimator bore is the pixel to pixel separation minus the septa's thickness. The optimal length of the longest and shortest collimator bore may then be selected by knowing the desired minimum and maximum resolution and the tradeoff between the resolution and sensitivity at the working distance from the organ of interest. To be able to pivot without collision with the cover (or the nearby detector) the entire moving part of the detector, including the sensor, the collimator, electronics and optional shielding fit within a circular cross-section region 181 (e.g., cylindrical shielding or cover) centered about the picturing point (such as shown, for example, in FIGS. 6, 9, 10, and 11). When using a wider detector, for example made of two or three side by side modules, a larger aspect ratio collimator (the ratio between the lengths of the longest and shortest collimator tubes) may be created, while efficiently filling the limiting circle.

It should be noted that different configurations of collimators may be provided. For example, in some embodiments, a collimator with a double pitch compared to the detector pitch may be provided (e.g., the pitch of collimator being twice the pitch of the detector). However, other different relative pitches may be provided. Using a collimator with a double pitch compared to the detector pitch allows for reducing the length of the collimator by half and reducing respectively the diameter of the detector unit. Thus, for example, the smaller detector unit allows the detector unit to be positioned closer to the subject before collision or colliding with adjacent detectors.

Figure 10:
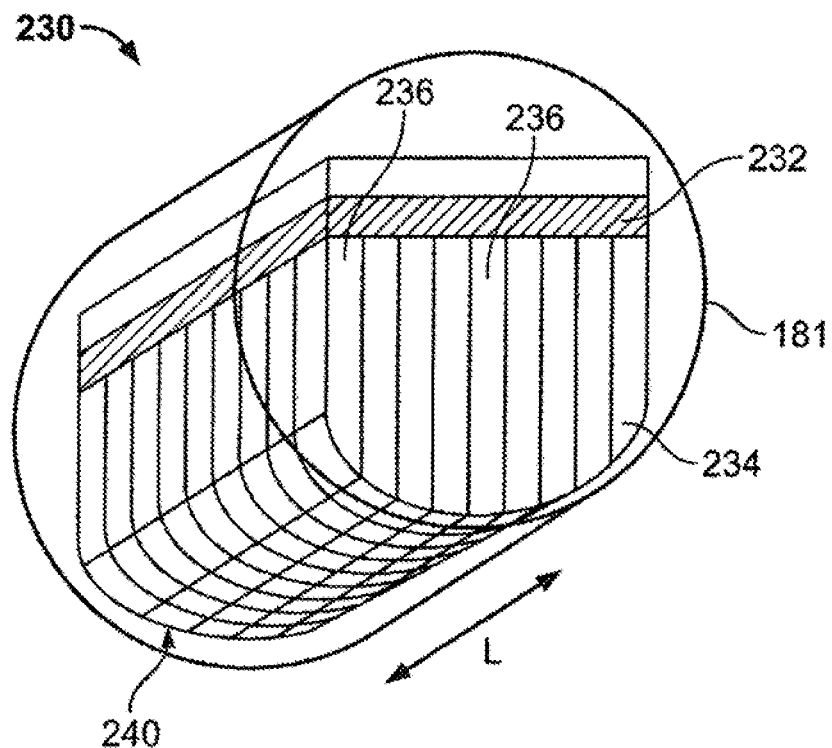
FIGS. 10 and 11 are diagrams illustrating a collimator arrangement in accordance with another embodiment.
Figure 11:
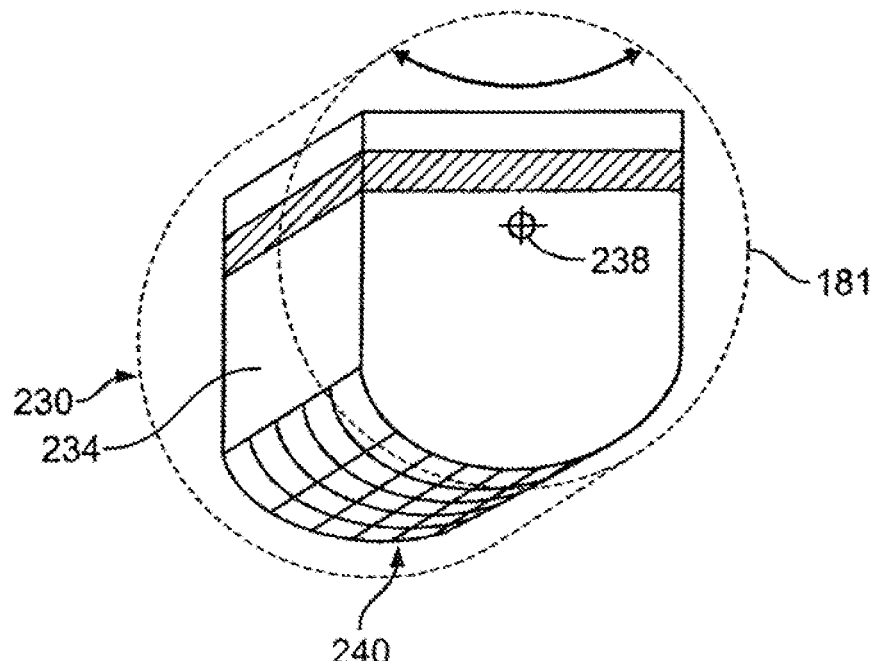

Different configuration of collimators also may be provided, such as curved in two-dimensions or three-dimensions. For example, as shown in FIGS. 10 and 11, which are isometric illustrations of FIGS. 6 and 9, a collimator 234 (which may be embodied as the collimator 172) may be provided that has varied bore length transverse to a longitudinal axis L of the detector 230. In this embodiment, the collimator bores 236 from front to back as viewed in FIGS. 9 and 10 have the same bore length, but the bore length is varied from side to side. An axis 238 of rotation may be provided as illustrated in FIG. 10 such that the curved face 240 rotates or swings about or parallel to the axis 238. However, in other embodiments, the axis 238 may be changed such that the curved face 240 may rotate transverse to the axis 238, such as if the axis 238 is positioned from one side to an opposite side of the detector 230 instead of from front to back as shown.

In some embodiments, a collimator 250 with a face 252 that curves from a center 254 in two-dimensions as shown in FIG. 12. For example, the curved face 252 is semi-spherical in this embodiment to allow swinging, for example, in two different directions (e.g., two orthogonal directions as illustrated by the arrows). This embodiment may be used, for example, for a detector pivoting in two directions.

Figure 13:
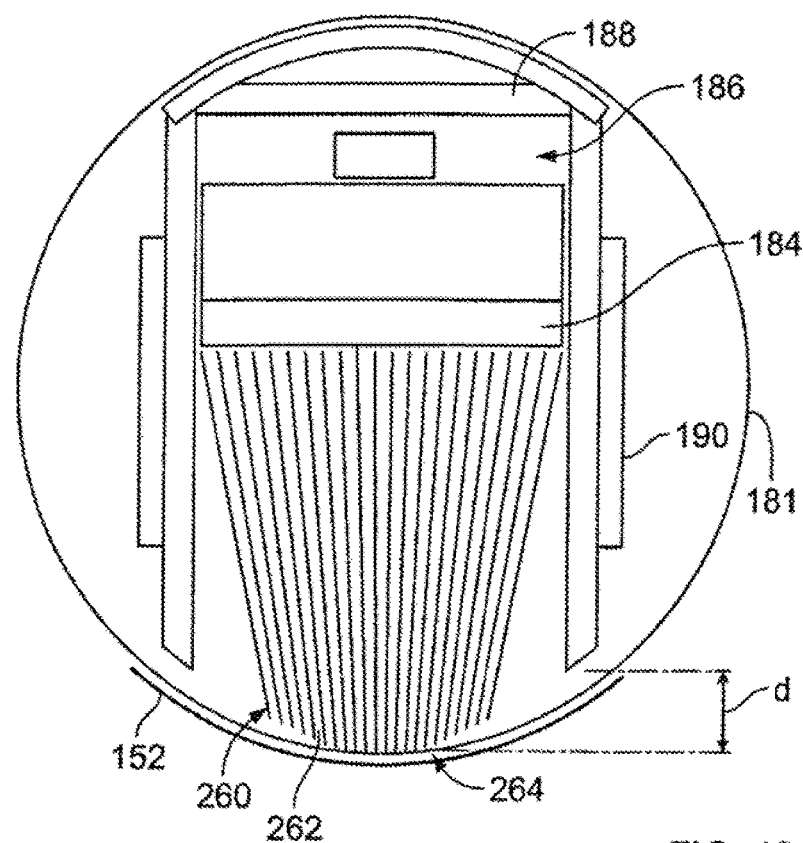
FIG. 13 is a diagram illustrating a collimator arrangement in accordance with another embodiment.
Figure 14:
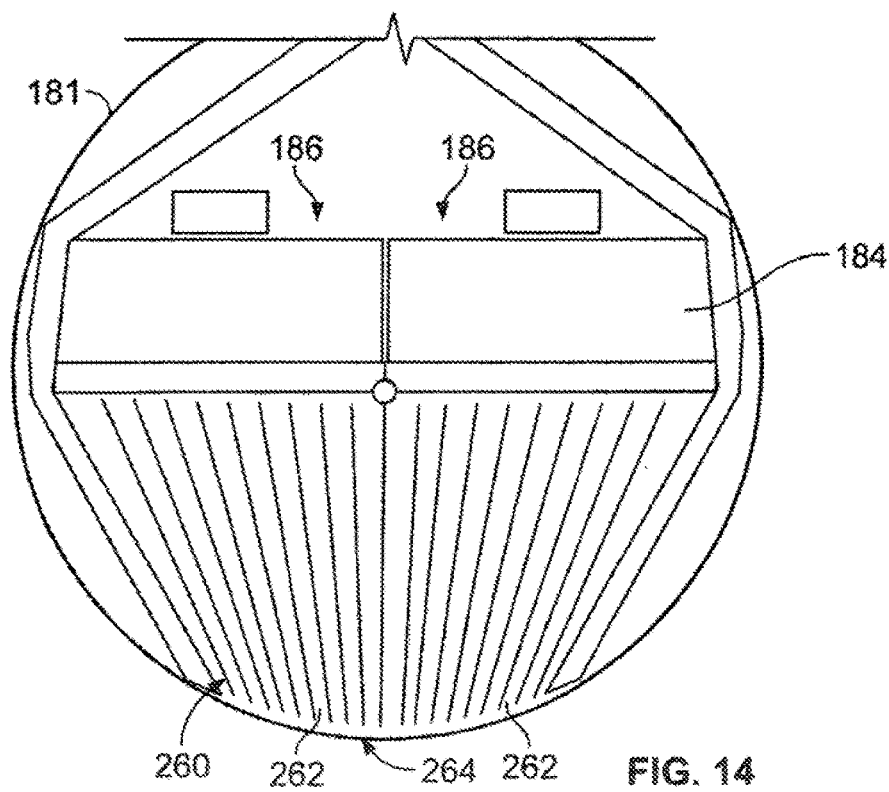
FIG. 14 is a diagram illustrating a collimator arrangement in accordance with another embodiment.

Other variations are contemplated. For example, as shown in FIGS. 13 and 14, a collimator 260 may be provided with variable length bores 262. However, in these embodiments, unlike the embodiments shown in FIGS. 5 and 8, respectively (where like numerals represent like parts), a fan-beam type collimation arrangement is provided instead of a parallel-hole arrangement. As can be seen, the bores 262 in this embodiment are angled towards a center region of the detector. Again, as should be appreciated, the bores 262 have different lengths to form a curved face 264. It should be noted that the fan beam configuration further reduces the distance from the face of the collimator to the patient at least for some portion of the face of the collimator and some pivot positions while efficiently remain within the circle 181 (e.g., limiting circle). This increase in resolution may contribute to better image quality. Additionally, as can be seen in FIG. 14, for a wide detector, the length of the tubes one the edges of the detector is similar to the length of the tubes in the center. Thus this configuration may provide a more even resolution across the detector, while at the same time reducing the distance to the patient.

Thus, various embodiments provide different motions of detector units, as well as different arrangements of collimators to allow the detector units to be positioned closer together and closer to the object to be scanned than conventional systems.

Figure 15:
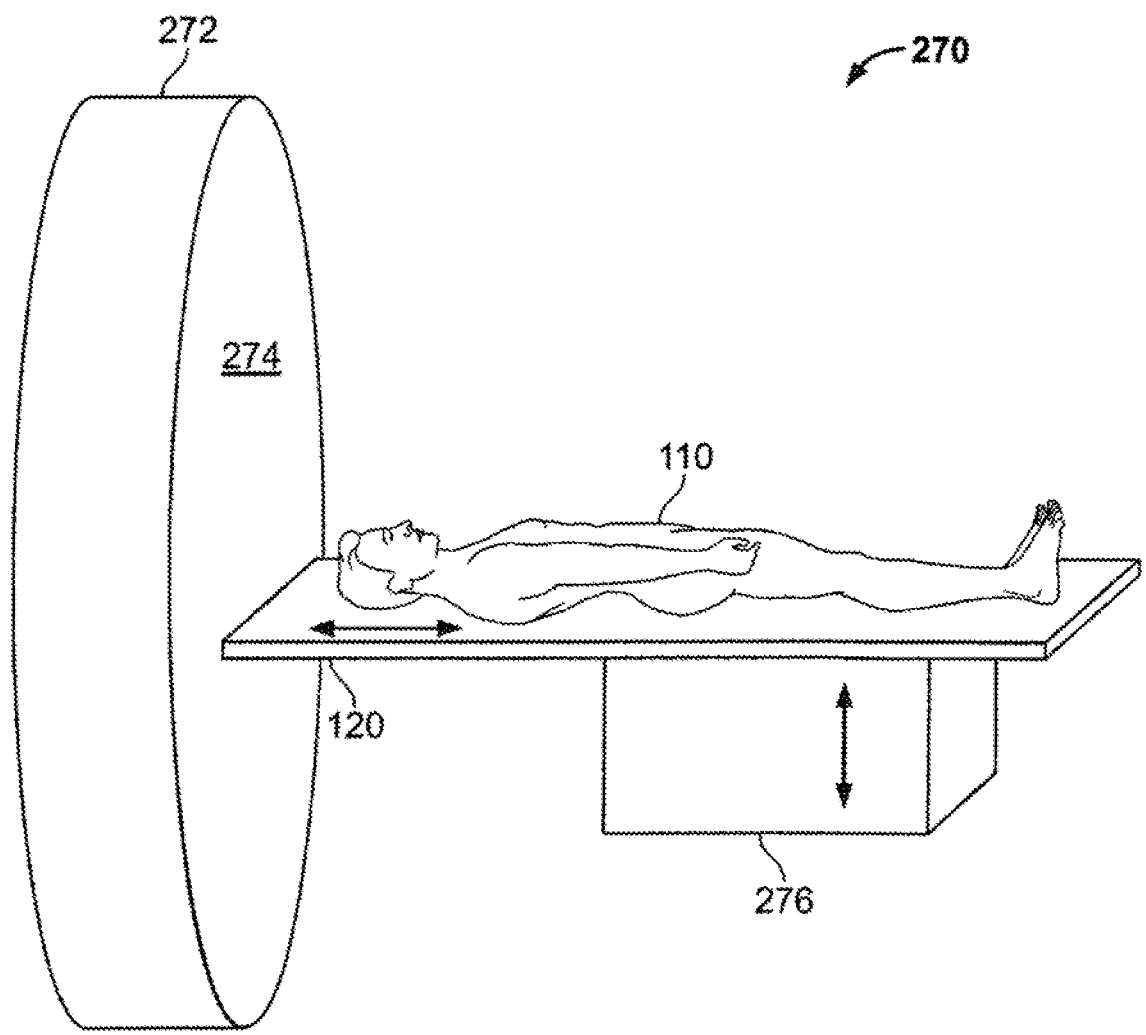
FIG. 15 is a diagram illustrating an imaging system in accordance with an embodiment in which one or more configurations of detectors may be implemented.

It should be noted that various embodiments may be implemented in different system configurations. For example, as shown in FIG. 15, an imaging system 270 may be provided that includes a gantry 272 with a bore therethrough. The gantry 272 may have coupled thereto different imaging detectors, for example, the imaging detectors 102 (as shown in FIG. 1). In this embodiment, the subject 110 is positioned on a patient table 120 that includes a support 276 (e.g., a patient table or bed mechanism) that allows movement of the patient table 120 as described herein. For example, the subject 110 may be moved upwards/downwards or left/right (along the examination axis) as viewed in FIG. 15. Thus, the subject 110 may be moved through the bore 274 and imaged as described in more detail herein, using one or more of the detector and/or collimator configurations described herein. Accordingly, in this embodiment, the system moves the subject 110 along the examination axis.

Figure 16:
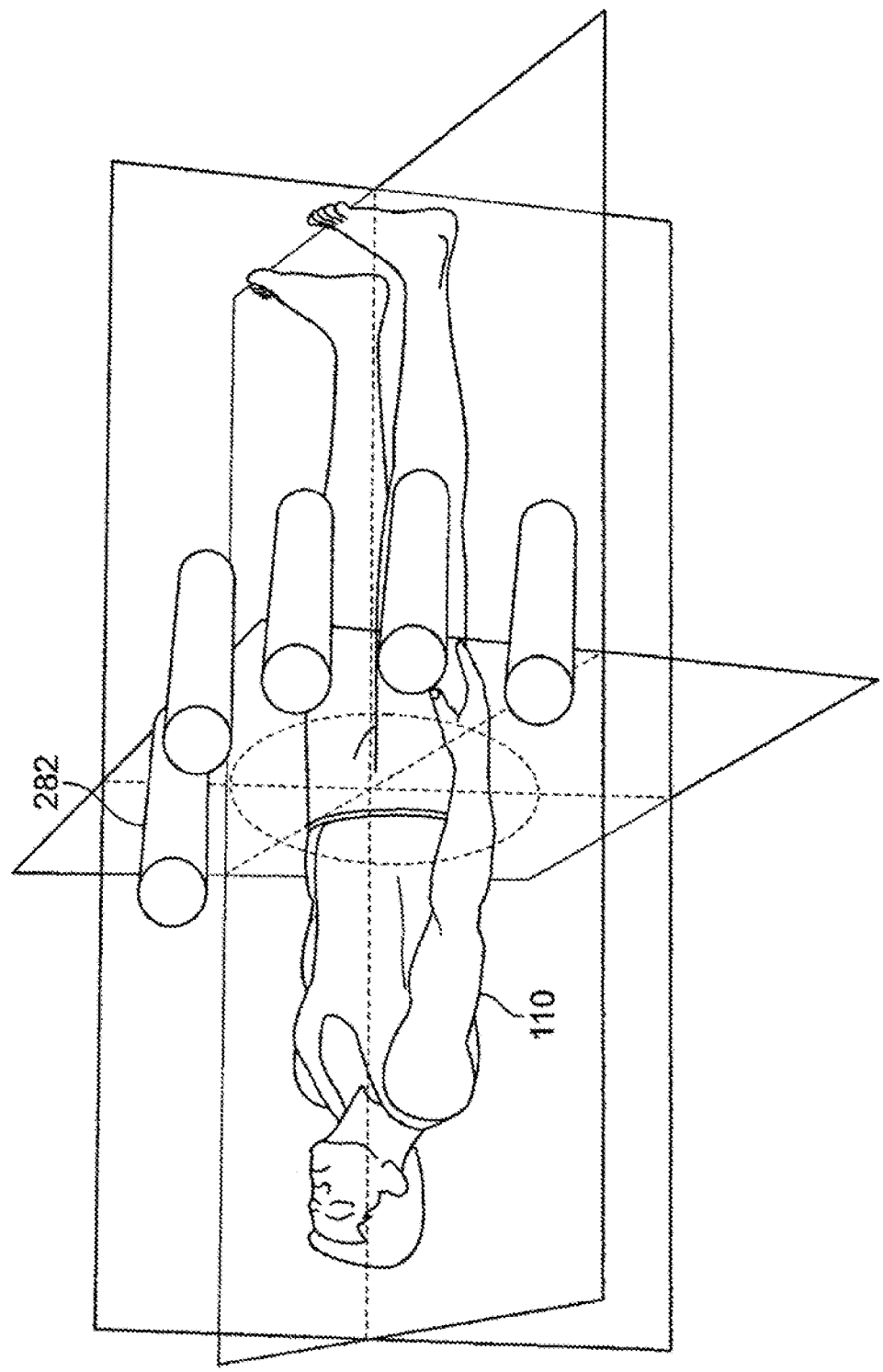
FIG. 16 is a diagram illustrating an imaging system in accordance with another embodiment in which one or more configurations of detectors may be implemented.

In another embodiment, for example, as shown in FIG. 16, and imaging system 280 may be provided wherein the imaging detectors 282 (which may be embodied as the imaging detectors 102 shown in FIG. 1) are positioned around at least a portion of the subject 110 (in some embodiments spaces partially or entirely around the subject 110). For simplicity and ease of description, only the detectors 282 and subject 110 are shown. However, one or more of the other system components as described herein are provided. The detectors 282 may be controlled or operated in this embodiment as described in more detail herein.

Thus, various embodiments may provide different configurations for positioning the detectors and/or subject 110 with respect to each other. The movement of the detectors may be, for example, radially or rotatably. In one embodiment, as shown in the imaging system 290 of FIGS. 17 and 18, a plurality of detectors 292 (e.g., the imaging detectors 102 shown in FIG. 1), are positioned and spaced evenly, such as distributed along a gantry evenly along the circumference of the gantry. For example, the detectors 292 are shown as spaced apart by 15 degrees, but other spacings may be provided. However, an uneven spacing and/or additional or fewer detectors 102 may be provided. As can be seen, the detectors 292 are movable radially inward and outward to position the detectors 292 adjacent to the subject 110 for imaging (shown in FIG. 18 in an imaging position or state). Thus, in this embodiment, the detectors 292 are shown in an outermost position in FIG. 17 and in an imaging position in FIG. 18. As should be appreciated, the detectors 292 are movable different distances (e.g., one or more detectors 292 moved different distances) depending on the size, shape, etc., of the subject 110.

Figure 17:
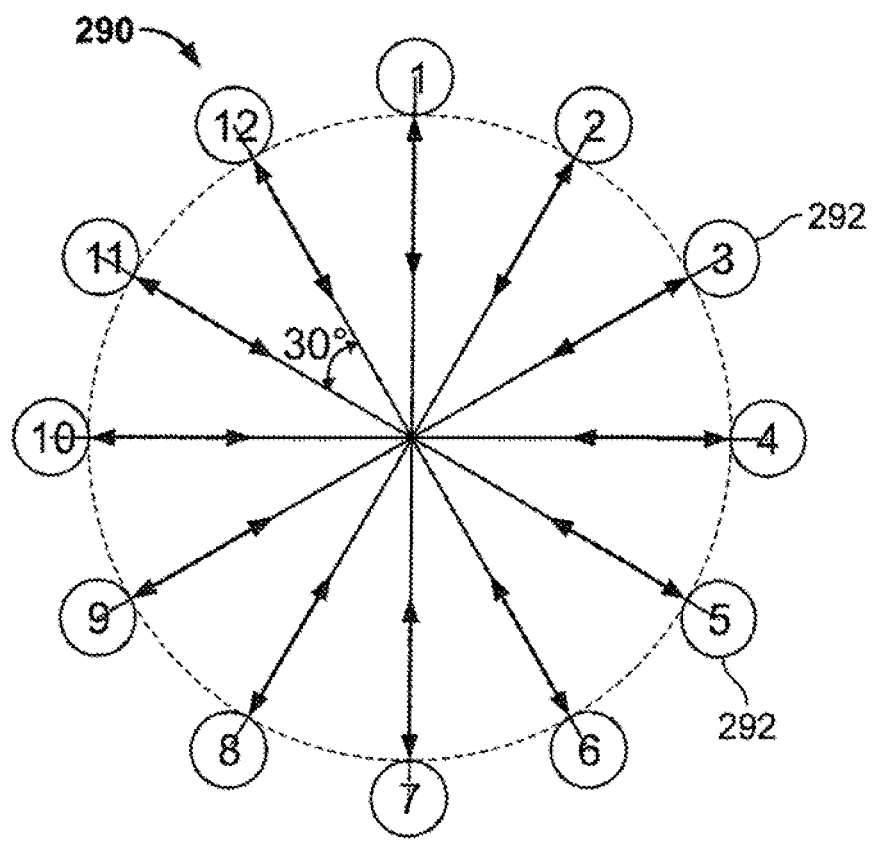
FIGS. 17 and 18 are diagrams illustrating motion of detectors in accordance with an embodiment.
Figure 18:
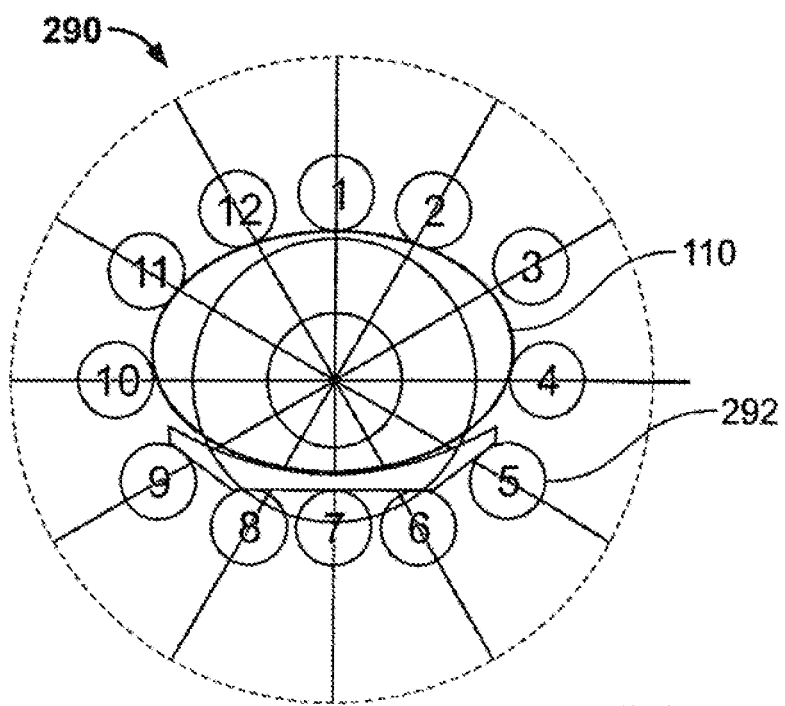
Figure 19:
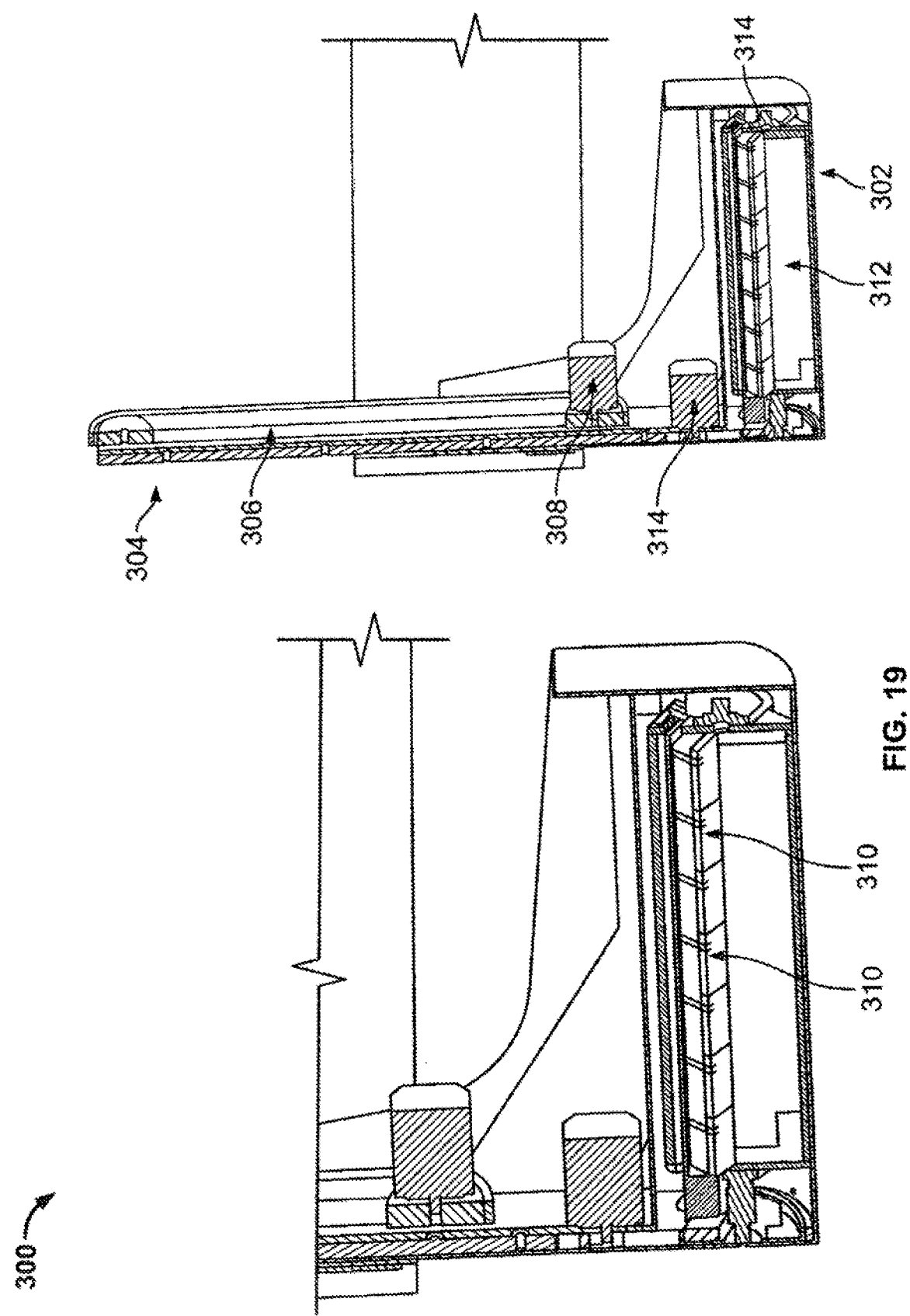
FIG. 19 is a diagram illustrating a detector arm configuration in accordance with an embodiment.

The mechanism or components to moving the imaging detectors in various embodiments may be provided using different arrangements. One arrangement 300 is shown in FIG. 19 illustrating an imaging detector configuration wherein a detector head 302 is mounted at one end of an arm 304 that includes a rail 306 to allow radial movement, such as shown in FIGS. 17 and 18. The movement may be controlled using a radial motion motor 308. The detector head 302 in this embodiment includes a plurality of imaging modules 310 (illustrated as CZT modules) that may be aligned in one or more rows (a single row is illustrated in the embodiment shown). As can be seen, a collimator 312 may be provided and coupled to one or more of the imaging modules 310. The collimator 312 may be provided as described herein. Additionally, the imaging modules 310 are coupled to a support 314 (e.g., a rod) that allows rotation or pivoting movement of the imaging modules 310 within the detector head 302. For example, a motor, such as a sweep motor 314 may be provided to control and move the imaging modules 310 to sweep across a region of interest (e.g., rotate or pivot a defined number of degrees).

Additionally, different configurations may be provided. For example, within a single cover or a single detector head, multiple detector units or modules may be provided. Additionally, one or more detectors may be fixed or mounted (or within) the patient table 120 or a support portion thereof.

Figure 20:
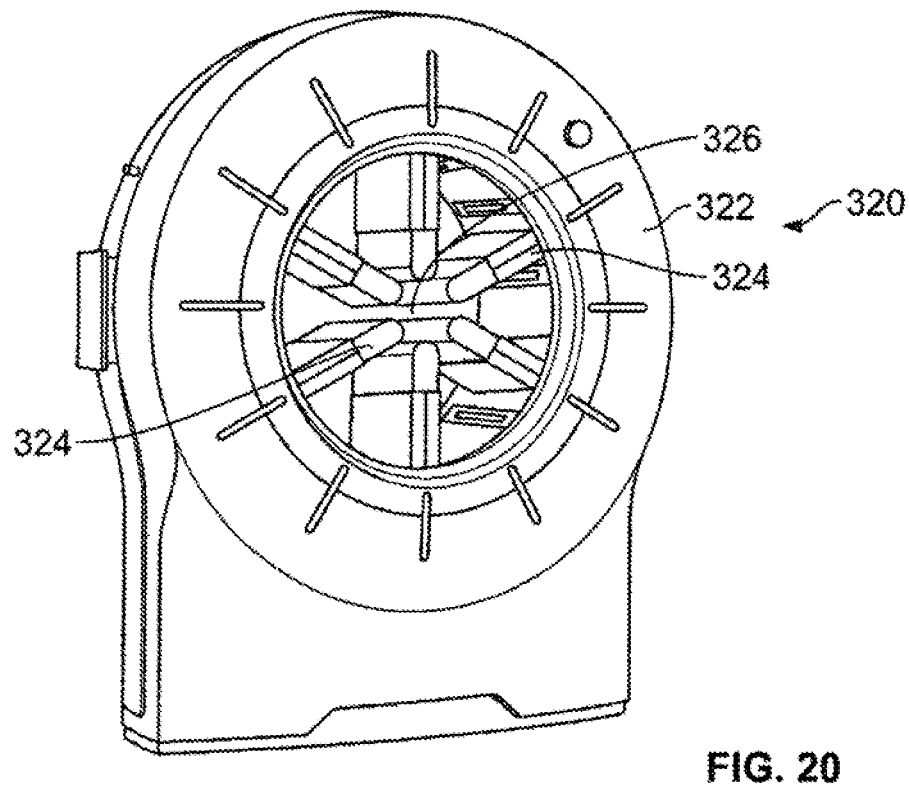
FIG. 20 is a perspective view of an imaging system in accordance with another embodiment.
Figure 21:
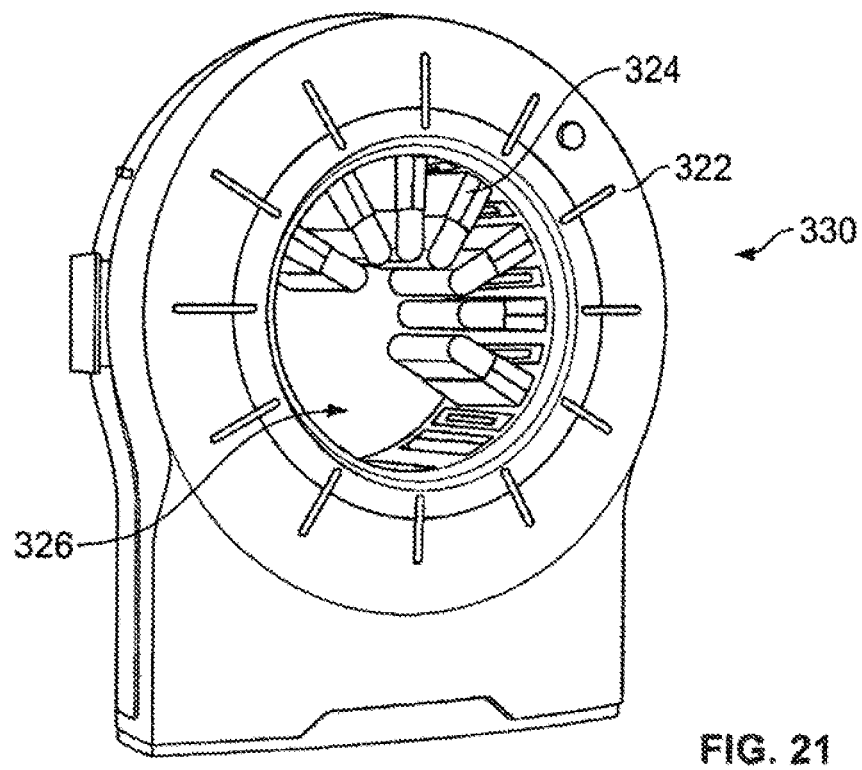
FIG. 21 is a perspective view of an imaging system in accordance with another embodiment.

It should be noted that a plurality of arms supporting the detector units may be provided in different configurations. For example, as shown in FIG. 20, a system 320 may be provided with a gantry 322 having a plurality of arms 324 (e.g., movable supports as described herein) that extend and/or are movable radially inward and outward from the gantry 292. It should be noted that the arms 324 are spaced apart circumferentially around the entire bore 326 in this embodiment. It also should be noted that additional or fewer arms and different spacing between arms 324 may be provided. The arms 324 may be movable as described herein and may be embodied as the detector carriers 116 (shown in FIG. 1) in some embodiments. Additionally, each arm 294 may support one or more detector units or modules (e.g., the detector units 114 shown in FIG. 1). Other variations include arms 324 that are provided along only a portion of the circumference of the bore 326 as illustrated in the system 330 of FIG. 21. It should be noted that although the arms 324 are illustrated along about 180 degrees, the arms 294 may be provided along more or less of the bore 326, such as more or less than 180 degrees. It should be noted that for the configuration shown in FIG. 21, rotations greater than 180 degrees may be used to provide imaging in both prone and supine positions of the subject 110. For example, in some embodiments, rotation of about 210 degrees is provided. However, the rotation may be more or less than 210 degrees as desired or needed.

Additionally, different configurations may be provided. For example, a linear type of design may be provided, such as described and shown in FIG. 11 in co-pending U.S. patent application Ser. No. 14/016,943, entitled "Methods and Apparatus for Imaging with Detectors having Moving Detector Heads", which is hereby incorporated by reference in its entirety.

Figure 22:
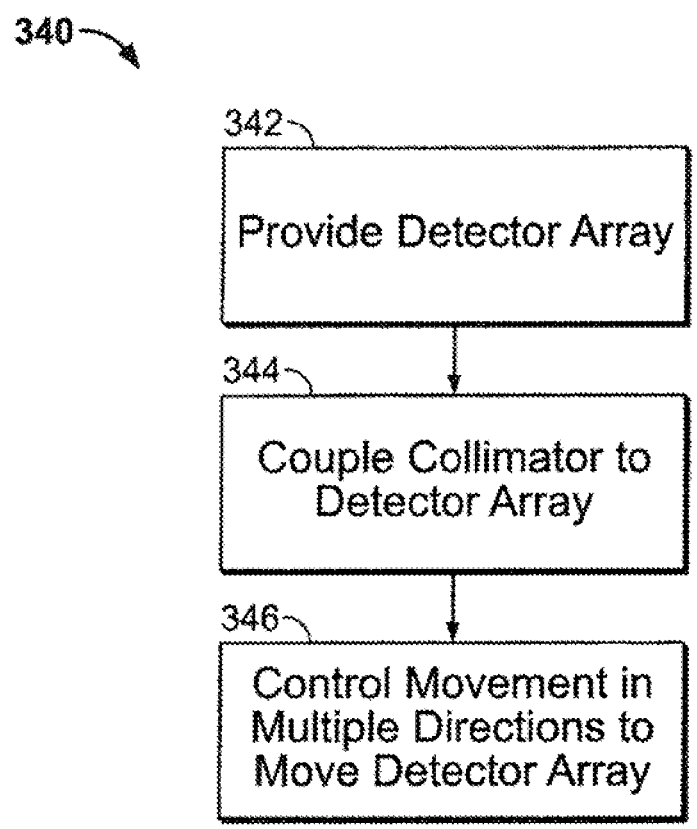
FIG. 22 is a flowchart of a method in accordance with various embodiments.

Various embodiments also provide a method 340 as shown in FIG. 22. The method 340 includes providing a detector array at 342, for example, a CZT array with associated electronics as described herein. A collimator is coupled to the detector array at 344. For example, a collimator with different length bores and/or a curved face as described herein may be used. However, in other embodiments, a planar face collimator may be used. The method 340 additionally includes controlling movement in multiple directions to move the detector array at 346. For example, as described herein, the detector array may be translated and rotated or swung concurrently.

Various embodiments also provide for focused scanning based on the portion of the body and/or shape of the body being scanned, for example providing adaptive scanning time per body part. For instance, in whole body scanning, different scanning times may be used for different body portions, such as the head, torso, legs, or arms, among others. Generally, slower scanning (thereby acquiring relatively larger amounts of information) may be performed for one or more body portions, while faster scanning (thereby acquiring relatively smaller amounts of information) may be performed for other body portions. Thus, scanning may be understood as focused on the portions of the body for which the slower scanning is performed. Thus, whole body scanning may be performed in a reduced amount of time by spending more scanning time at those portions of the body for which improved imaging is required and less scanning time at less critical body portions, or body portions of less interest (e.g., less clinical interest). Further, information from other modes (e.g., CT, manual mode) may be used to further improve scanning time. Additionally or alternatively, focused scanning may be performed for one or more organs within one or more slices of an image. For example, information on organ localization may be obtained from another modality, such as CT, and slower scanning may be performed on the portion within a slice of the organ of interest, and faster scanning performed on portions within the slice outside of the organ of interest.

For example, in various embodiments, a plurality of detector units (see, e.g., FIG. 1 and related discussion) of an imaging system may be configured to acquire SPECT data, with the system also including a CT imaging unit that is configured to acquire CT image information. A controller (e.g., pivot controller 138) may be utilized to control the pivoting or rotation (and/or other movement) of the detector units to focus at least one of the detector units on a first region or portion (e.g., a region of interest), with the movement of the detector unit controlled automatically using CT image information acquired by the CT imaging unit.

For example, CT image information may be acquired and reconstructed to provide a 3D image. Additionally or alternatively, a scout scan may be performed using a different modality. Then, using the 3D image, a "target organ recognition and localization" may be performed, in which the target organ (or organs) is identified and a volume of interest (VOI) that includes the target organ (or organs) is defined. Thus, a volume of interest may correspond to one or more organs or body portions (e.g., legs or kidneys, among others). An identified volume may also include a safety margin around the VOI (or VOI's). The identification, or recognition and localization, of the target organ (or organs) may be performed using one or more techniques. For example, automatic image processing software, for example based on a known general shape and density of the target organ, and/or the general shape and density of non-target organs near the target, may be utilized. As another example, semi-automatic image processing software, in which a user input is used to point at a target organ, may be employed. As yet one more example, manual identification (e.g., by an operator identifying locations on the boundaries of the VOI) may be employed. Generally, the location and size of the identified VOI is used to guide the scanning detector units such that a majority of scanning time of at least one detector (e.g., a majority of detectors) is spent viewing or scanning the VOI. In some embodiments, all or substantially all of the viewing time may be spent on the VOI.

Thus, scanning time may be focused on a body portion or VOI. This focusing in various embodiments may permit not only focusing on a specific organ within the body, but also may be used to define an angular swinging (or rotating) range (and/or number of steps or distance between steps over a range) respective to different body parts being scanned (e.g., head, torso, or legs, among others). For example, in a SPECT camera based on swinging (or otherwise rotating) detector heads, the time to obtain a clinically useful image is strongly dependent on the size of the scanner organ or body part. Generally, an imaged VOI may extend over a longitudinal range equal to the length of the scanning heads (or a multiple of heads, if several heads are used). In a transverse direction, the VOI is limited to the extent of the body part or only to an organ of interest (OOI), whichever is smaller. In a whole body SPECT a patient may be moved with respect to the camera and a 3D image of large sections (or the entire body) may be obtained. As the patient is moved (e.g., via table controller 134), the configuration of the heads around the patient, and the range of swinging or other rotation of the heads may be controlled according to body part being scanned in order to achieve fast scanning of the currently scanned region of interest. In some embodiments, scanning time may be limited to the minimum that ensures adequate clinical image quality or to acquire adequate background imaging information. This time may be influenced by the type of organ, each having a different volume and requiring a different angular swinging or rotation range. The overall scanning time may be shortened and optimized per body shape by controlling the swinging or rotation of the heads to perform increased scanning at one or more volumes of interest and decreased scanning at portions of the body of lesser interest. The shape of the body, as also indicated elsewhere herein, may also be determined from other modalities such as CT, from information from a body contouring device, using a manual clearance learning mode, or by a different device or technique providing information on body shape.

Figure 23:
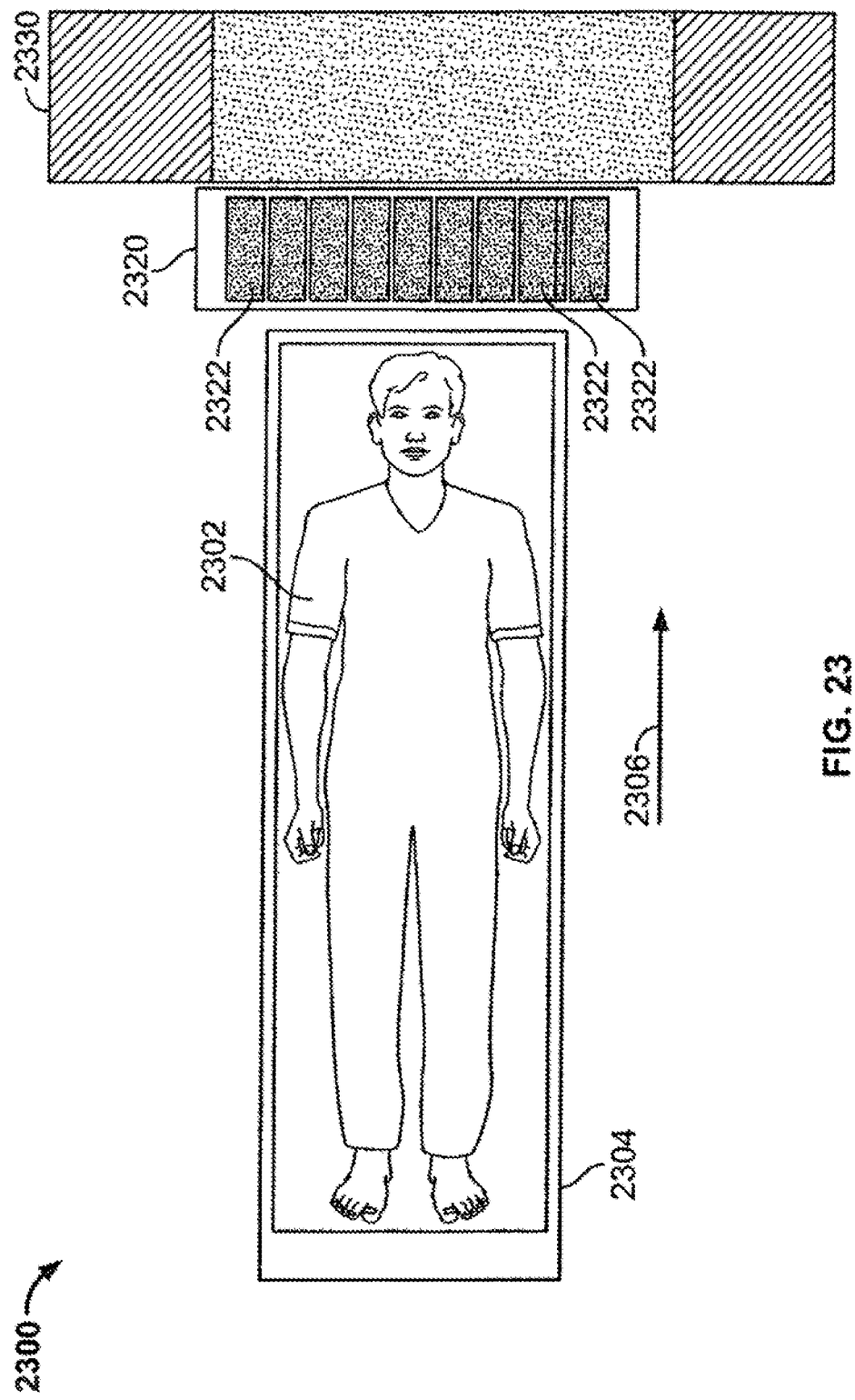
FIG. 23 illustrates an imaging system in accordance with various embodiments.
Figure 24:
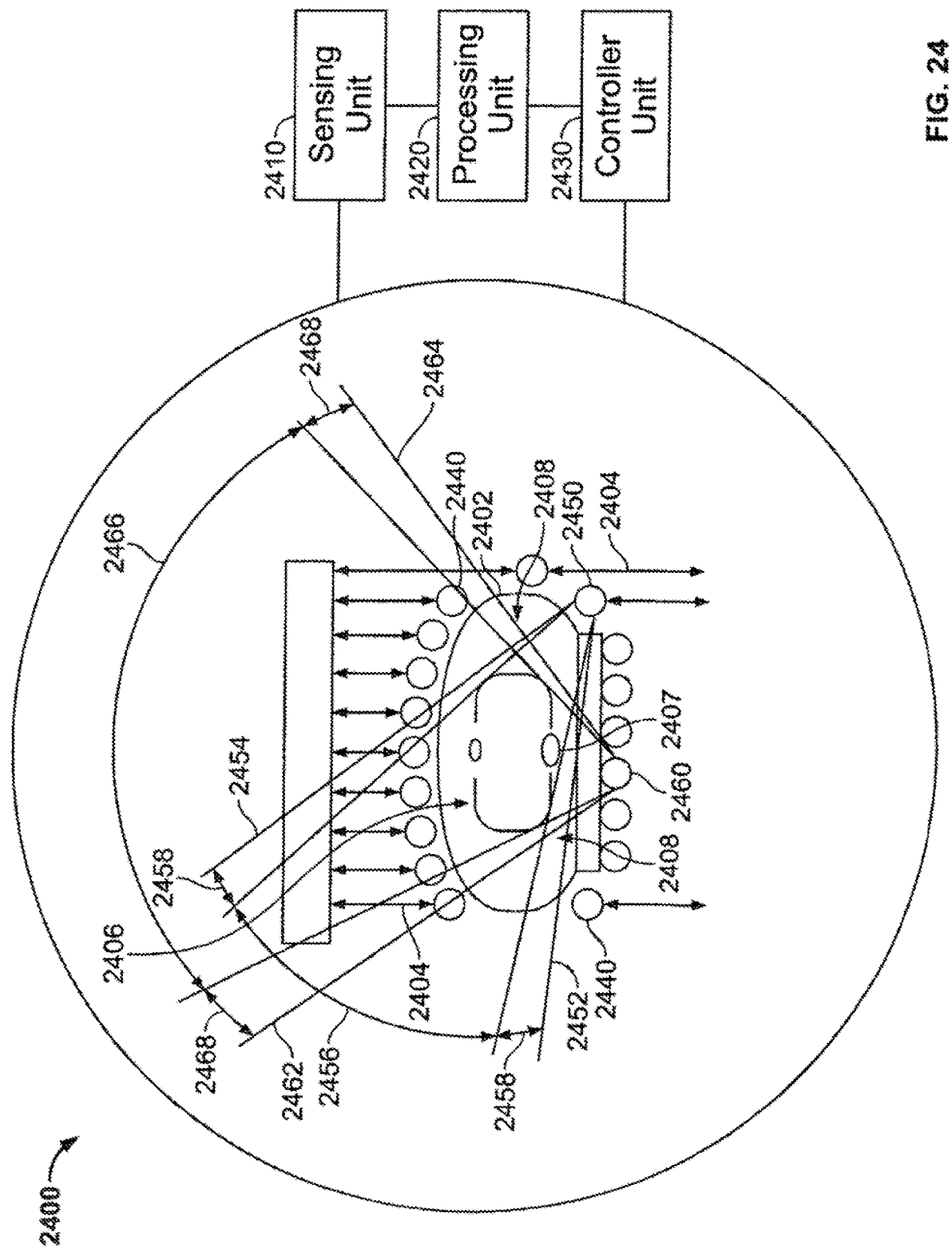
FIG. 24 illustrates an imaging system in accordance with various embodiments.
Figure 25:
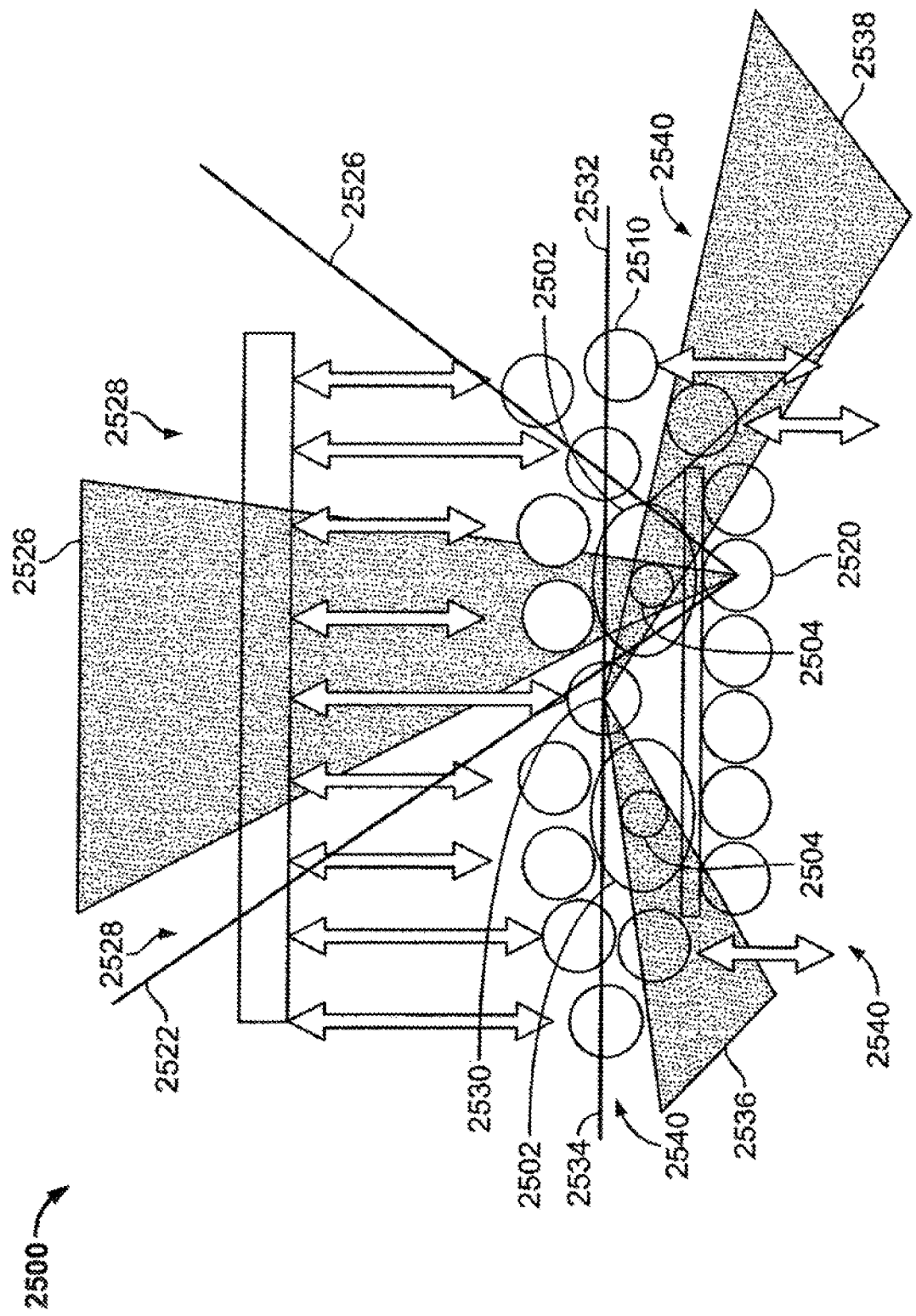
FIG. 25 illustrates an imaging system in accordance with various embodiments.

FIGS. 23-25 illustrate example embodiments of systems that provide for focused scanning. FIG. 23 illustrates an imaging system 2300 in accordance with various embodiments. The imaging system 2300 is used to image a patient 2302. It may be noted that other objects may be imaged in alternate embodiments. The imaging system 2300 includes a bed 2304 configured to support and position the patient 2302, with the bed articulable in a bed motion direction 2306. The imaging system 2300 also includes a gantry 2320 including detectors 2322. The detectors 2322 may be configured to rotate with the gantry 2320 and/or independently of the gantry 2320 (see, e.g., FIG. 1 and related discussion). The imaging system 2300 also includes an imaging unit 2330 configured to obtain object information of the object being scanned (e.g., patient 2302). In the illustrated embodiment, the imaging unit 2330 is configured as a CT scanning unit. As discussed herein, the imaging unit 2330 (e.g., CT scanning unit) may be used to identify a portion of the patient 2302 for focused scanning.

FIG. 24 illustrates an example of focused scanning. In FIG. 24, an imaging system 2400 is depicted including a sensing unit 2410, a processing unit 2420, and a controller 2430. The imaging system 2400 includes a plurality of detector units 2440 used to scan an object 2402. The detector units 2440 are rotatable about the respective centers of the detector units, and may also translate linearly in direction 2404. Alternatively, in various embodiments, the detector units 2440 may be translated radially inward toward an object to be scanned instead of linearly as shown in FIG. 24. The sensing unit 2410, which may be configured as a CT scanning unit (e.g., imaging unit 2330), is configured to obtain object information corresponding to the object 2402 to be imaged. The object information, for example, may describe, depict, or otherwise correspond to the shape and/or internal structure of the object 2402. The processing unit 2420 is operably connected to the sensing unit 2410 and obtains the object information from the sensing unit 2410. The processing unit 2420 in various embodiments is configured to determine, based on the object information, at least one first region or portion of the object for more focused scanning, and to determine at least one second region or portion of the object, with the at least one first portion being identified for more focused scanning relative to the at least one second portion.

As used herein, focused scanning may be understood as including acquiring relatively larger amounts of information for a given range of an object than for other ranges for which less focused or un-focused scanning is performed. For example, a larger amount of time may be spent acquiring information for focused scanning of a first range than for scanning of a similarly sized second range. The first range for focused scanning may correspond to a volume of interest, with the second range corresponding to a volume of lesser interest. For example, the first range may include a volume of interest selected or determined based on clinical interest along with a buffer volume on one or more sides of the volume of interest. As used herein, a volume of interest may be understood as being of clinical interest for a particular application with the lesser interest being of lesser clinical interest (e.g., the bones of legs may be identified as volumes of interest for a bone scan, with the muscles of the legs identified as a volume of lesser interest). In some embodiments, scanning information from a volume of interest is obtained to image a portion of the body being analysed or diagnosed, while one or more volumes of lesser interest may be identified and scanned to, as examples, provide for a more natural appearance of the image, provide context for the image, provide improved or easier registration with an additional image, and/or provide for easier or improved navigation within the image. Additionally or alternatively, regions or portions for focused scanning may be determined or identified based on characteristics such as uptake and/or attenuation. For example, a region that has greater attenuation may be selected as a first region for focused scanning, while a different region having less attenuation may be selected as a second region for less focused scanning. As another example, a region that is characterized by lower uptake (e.g., uptake of an administered radiopharmaceutical for imaging) may be selected as a first region for focused scanning, while a different region by higher uptake may be selected as a second region for less focused scanning. For instance, in a brain scan, the skull (e.g., cortex) and striatum (deep brain structure) may both be of clinical interest. However, more focused scanning may be performed on the striatum and less focused scanning may be performed on the skull because the skull is more shallow.

In the example provided by the embodiment illustrated in FIG. 24, the first range for focused scanning includes a portion of interest (e.g., a portion of clinical interest for a given application), while the second range is defined by a portion of lesser interest (e.g., lesser clinical interest for the given application). Thus, in the illustrated embodiment, the processing unit 2420 is configured to determine, based on the object information, at least one portion of interest of the object 2402 and at least one portion of lesser interest of the object 2402. For example, in the illustrated embodiment, the object 2402 includes a volume of interest 2406 and an area of lesser interest 2408. For example, the object 2402 may be a torso of the patient, and the volume of interest 2406 may include the bones 2407 of the torso, while the volume of lesser interest 2408 may lie outside of the outline of the bones 2407. The volume of interest 2406 (e.g., bones 2407) may be determined using information from the sensing unit 2410 (e.g., using information from a CT or other modality scan to identify and locate the bones). While the volumes 2406 and 2408 are selected or determined based on clinical interest in the illustrated embodiment, in other embodiments the volumes 2406 and 2408 may be selected alternatively or additionally based on attenuation and/or uptake, for example.

The depicted controller 2430 is configured to control a rotational movement of the detectors 2440. For example, each detector 2440 may be rotatable at a sweep rate from a first position to a second position defining a range of view of the object 2402. In the illustrated embodiment, the controller 2430 is configured to rotate at least one detector 2440 from the first position to the second position at an uneven sweep rate. In FIG. 24, the detectors 2440 are configured to rotate independently of the gantry. The detectors 2440 may rotate, swing, or pivot about a pivot point. In the illustrated embodiment, each detector 2440 is configured to rotate about the center of the particular detector. The controller 2430 may receive information describing one or more volumes of interest from the processing unit 2420, and control the uneven sweep rate to vary during the rotation from the first position to the second position such that a larger amount of scanning information is obtained for the volume of interest 2406 than for the volume of lesser interest 2408. For example, the sweep rate may be relatively slower during viewing of the volume of interest 2406 and relatively faster during viewing of the volume of lesser interest 2408.

While each detector 2440 (or a fraction of the total numbers of detectors 2440) may be thus controlled in various embodiments, the rotation of two detectors only will be discussed in connection with FIG. 24 for clarity of illustration. As seen in FIG. 24, a first detector 2450 may be rotated from a first position 2452 to a second position 2454. A scan range of interest 2456 is defined that passes through and includes the volume of interest 2406. Ranges of lesser interest 2458 lie on either side of the range of interest 2456. The sweep rate may be varied to be slower during the scanning of the range of interest 2456, to acquire a relatively large amount of information (e.g., photon counts) for the range of interest 2456 than from the ranges of lesser interest 2458, which are less useful for providing a useful image of the volume of interest 2406.

Similarly, as shown in FIG. 24, a second detector 2460 may be rotated from a first position 2462 to a second position 2464. A scan range of interest 2466 is defined that passes through and includes the volume of interest 2406. Ranges of lesser interest 2468 lie on either side of the range of interest 2466. Again, the sweep rate may be varied to be slower during the scanning of the range of interest 2466, to acquire a relatively large amount of information for the range of interest 2466 than from the ranges of lesser interest 2468. Thus, focused scanning may be provided for acquiring relatively large amounts of information for the ranges and volumes of interest and relatively lesser amounts of information for ranges and volumes of lesser interest, thereby making more efficient use of scanning time and/or reducing scanning time while improving useful image quality. It may be noted that in some embodiments, one or more detectors may be rotated or controlled to acquire information only for a range and volume of interest, and not to acquire information of other ranges or volumes. It may also be noted that different detectors may be controlled to focus on different VOIs within the body.

FIG. 25 illustrates an example scenario having more than one volume of interest. In FIG. 25, an imaging system 2500 is depicted for performing a focused scan of legs 2502. In various embodiments, other groups of organs or body portions may be identified additionally or alternatively as volumes of interest for focused scanning. The imaging system 2500 may be generally similarly in various respects to imaging systems discussed herein, such as the imaging system 2300 and the imaging system 2400. Due to the shape of the legs 2502, as the individual detectors are positioned, one or more of the detectors may be used to acquire scanning or imaging information of both legs, one or more of the detectors may be used to acquire information of one leg, and one or more of the detectors may be idle and not acquire information. In the illustrated embodiment, a first detector 2510 is idle, a second detector 2520 acquires information of one leg, and a third detector 2530 acquires information of both legs.

In the illustrated embodiment, volumes of interest 2504 include the bones of the legs 2502. The second detector 2520 may be rotated from a first position 2522 to a second position 2524. A scan range of interest 2526 is defined that passes through and includes the volume of interest 2506. Ranges of lesser interest 2528 lie on either side of the range of interest 2526. The sweep rate may be varied to be slower during the scanning of the range of interest 2526, to acquire a relatively large amount of information for the range of interest 2526 than for the ranges of lesser interest 2528.

The third detector 2530 may be rotated from a first position 2532 to a second position 2534. A first scan range of interest 2536 is defined that passes through and includes the bone of one leg, and a second scan range of interest 2538 is defined that passes through and includes the bone of the other leg. Scan ranges of lesser interest 2540 are disposed to the left of the first scan range of interest 2536, to the right of the second scan range of interest 2538, and between the first scan range of interest 2536 and the second scan range of interest 2538. The sweep rate of the third detector 2530 in the illustrated embodiment may be controlled to provide focused scanning of the volumes of interest 2504, for example by providing a lower sweep rate during rotation over the ranges of interest 2536, 2538 and a faster sweep rate during rotation over the ranges of lesser interest 2540. Thus, a relatively larger amount of information may be acquired for the volumes of interest 2504 than for volumes of lesser interest, thereby making efficient use of scanning time. As shown in FIG. 25, different detectors (e.g., second detector 2520 and third detector 2530 may be controlled differently and/or cover different portions of a subject being imaged. Further, in some embodiments, information from a range between the legs (e.g., a range including air but no body tissue or little body tissue) may be disregarded or not collected, while information from ranges of lesser interest that pass through body tissue may be used, for example in artifact correction and/or to provide a low resolution image providing for improved navigation and/or registration to other images.

In some embodiments, focused scanning may be performed using information from only a portion of one or more detector units (e.g., a high resolution portion), while in other embodiments information from the entire detector unit may be utilized. In some embodiments, different weighting may be given to information from different parts of a given detector unit during reconstruction (e.g., higher weighting given to information collected with a higher resolution portion of a detector unit). Further, the sweep rate of swinging, pivoting, or rotating the detector units may be controlled based on portion of the detector unit. For example, a high pivoting or sweep rate may be used while a high resolution part of a detector unit is viewing parts of a patient outside of a VOI, while a slower pivoting or sweep rate may be used while the high resolution part of a detector unit is scanning the VOL Further, the sweep rate and/or rotational range over which a particular detector is rotated may be controlled differently for different detectors.

As indicated herein, in some embodiments, the focused scanning may be performed to acquire information only for a volume (or volumes) of interest. However, in other embodiments, information may be acquired for additional volumes as shown in connection with FIGS. 24 and 25. It may be noted that while a reconstructed 3D image of the VOI may be required or desired clinically, imaging portions of the patient outside of the VOI may be advantageous or desirable as well. For example, reconstruction artifacts may be caused by radiation sources outside of the VOI which are viewed by only some of the detector units and not by others, which may cause inconsistency in the reconstruction process. However, while high resolution and low noise is desired for the VOI reconstruction, reconstruction of the sources outside the VOI may be done with low image quality (i.e., with higher noise and/or lower resolution) in order to avoid and/or correct artifacts. Further, displaying, with an image, areas outside of the VOI may provide for a more natural appearance of the image, and/or provide context for the image, and/or allow for improved or easier registration (e.g., with a CT image), and/or provide for easier or improved navigation within the image.

It may be noted that the sweep rate may be varied using one or more techniques. As one example, the sweep rate may be varied by non-uniform angular sampling (e.g., varying a rotational speed or rate of rotation) while maintaining a uniform or constant time per view. As another example, the sweep rate may be varied by non-uniform time per views while maintaining uniform or constant angular sampling. As one more example, non-uniform angular sampling may be combined with non-uniform time per view. It may further be noted that in various embodiments the sweep rate may be varied during a substantially continuous rotational movement (e.g., completely devoid of pauses or interruptions in rotation, or with insubstantial pauses in rotation), or, alternatively, during a "step and shoot" acquisition (e.g., one or more detector units rotated in a series of discrete steps, with information acquired during periods of no rotation between rotating from one step to an adjacent step). Further still, in various embodiments, the steps may be defined by a change of angle between steps or by a total number of angular steps provided over a given range.

It may be noted that, in some embodiments, only a relatively small body portion (e.g., one leg only instead of two as shown in FIG. 25) may be scanned. To scan only one leg, the positioning and the scanning ranges of the detectors may be adjusted accordingly. In this case, some of the detector units may optionally be idle during the scan. Similarly, when only part of the torso, for example, a shoulder, or only one arm, as another example, is to be scanned, the positioning and the scanning ranges of the detectors may be adjusted accordingly, and some detectors may optionally be idle during the scan.

Figure 26:
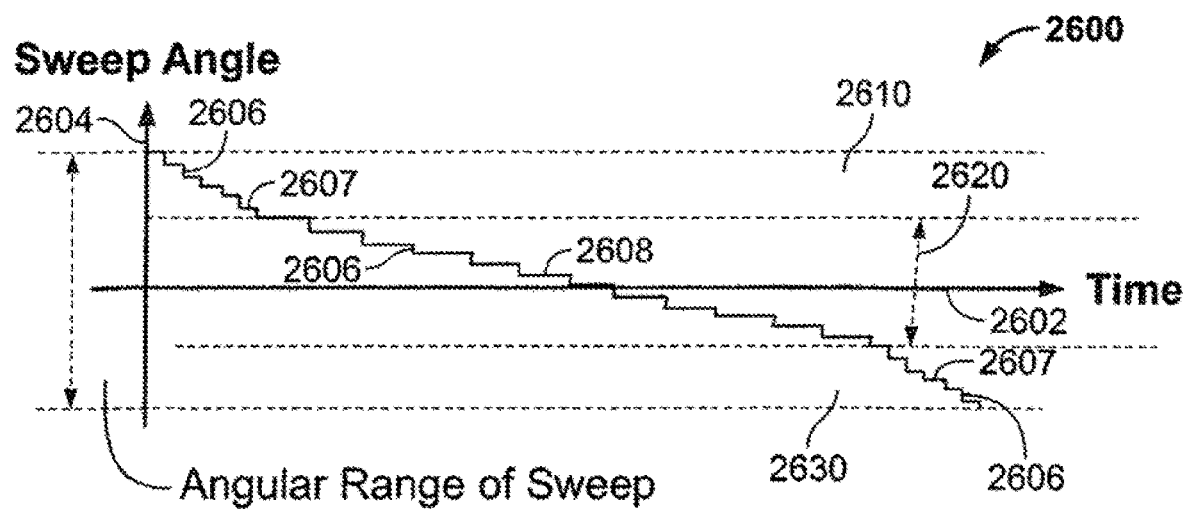
FIG. 26 illustrates an example of varying sweep rate in accordance with various embodiments.

FIG. 26 illustrates an example of varying sweep rate in accordance with various embodiments. In FIG. 26, a curve 2600 depicts rotation of a detector along a horizontal axis 2602 corresponding to time and a vertical axis 2604 corresponding to sweep angle, or rotation or pivoting of the detector. As seen in FIG. 26, the detector is rotated from a first range 2610 through a second range 2620 to a third range 2630. The second range 2620 corresponds to a range of interest (e.g., scan range of interest 2466) or range of focus, while the first range 2610 and the third range 2630 correspond to ranges of lesser interest (e.g., ranges of lesser interest 2468). FIG. 26 provides an example of "step and shoot" acquisition, with the detector rotated in a series of discrete steps between information acquisition periods. In the depicted embodiment, the sweep step 2606, or angular displacement between each acquisition step, remains the same for the first range 2610, the second range 2620, and the third range 2630. However, the dwell time, or time spent acquiring information at a given step, varies. In the illustrated embodiment, the dwell time 2607 is about the same for the first range 2610 and the third range 2630. The dwell time 2608 for the second range 2620 is longer than the dwell time 2607. Thus, more time is spent acquiring information for a given step during the range of interest than other ranges. By way of example and not limitation, the dwell time for one or more steps of the range of interest may exceed the dwell time for other ranges by a factor of about 2, 3, 5, or the like. The variation in dwell time may be selected to provide sufficient information acquisition during the range of interest to provide clinically useful imaging results, while providing, for example, sufficient information during other ranges to provide adequate artifact correction and/or registration with images obtained using other modalities. FIG. 26 provides an example of non-uniform angular sampling with a uniform or constant time per view. It may be noted that the scan range may optionally divided to more or less than three sub-ranges with different scanning rates. For example a sequence of five sub-ranges in the following order may be employed: very-fast; fast; slow; fast; very-fast. As the speeds or sweep rates employed in the previous example are symmetric about a central sub-range (e.g., the third of the five sub-ranges in a sequence of five) in the sequence, the previous example may be understood as symmetric; however, in other embodiments, non-symmetric division or sequencing of sub-ranges may be used.

Figure 27:
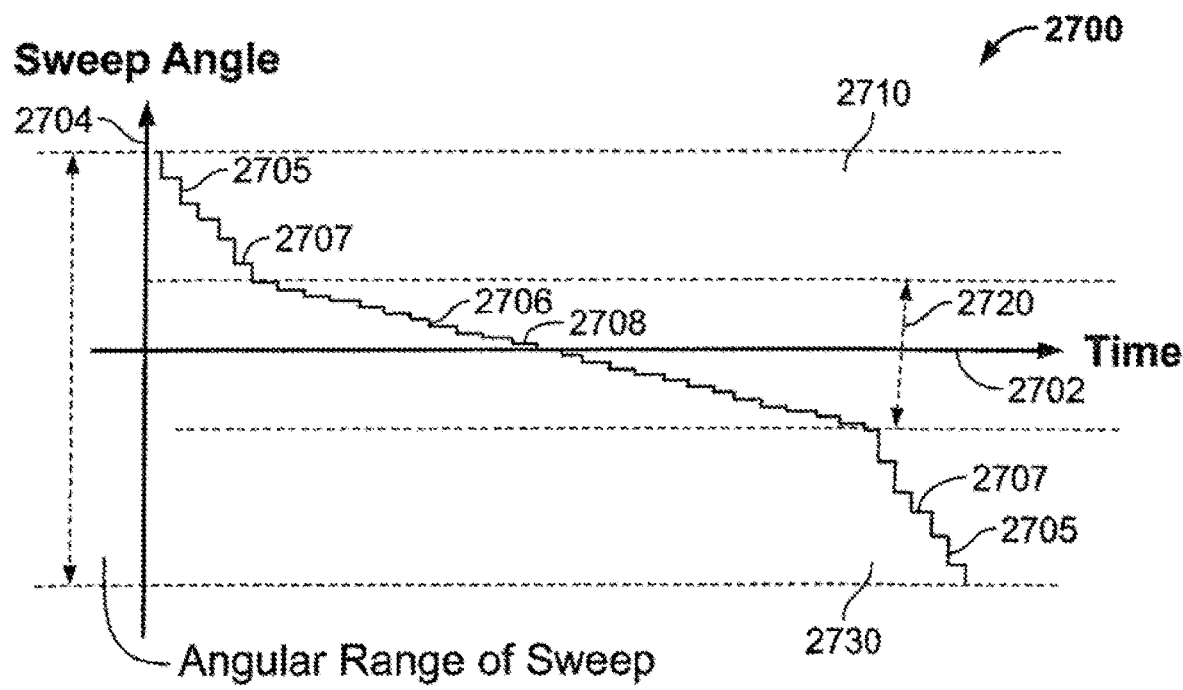
FIG. 27 illustrates another example of varying sweep rate in accordance with various embodiments.

FIG. 27 illustrates another example of varying sweep rate in accordance with various embodiments. In FIG. 27, a curve 2700 depicts rotation of a detector along a horizontal axis 2702 corresponding to time and a vertical axis 2704 corresponding to sweep angle, or rotation or pivoting of the detector. As seen in FIG. 27, the detector is rotated from a first range 2710 through a second range 2720 to a third range 2730. The second range 2720 corresponds to a range of interest or range of focus, while the first range 2710 and the third range 2730 correspond to ranges of lesser interest. Like FIG. 26, FIG. 27 provides an example of "step and shoot" acquisition, with the detector rotated in a series of discrete steps between information acquisition periods. In the depicted embodiment, the sweep step, or angular displacement between each acquisition step varies, as does the time spent acquiring information at a given step. The depicted sweep step 2705 for the first range is about the same as the sweep step 2705 for the third range 2730. However, the sweep step 2706 for the second range 2720 is smaller than the sweep step 2705, resulting in a greater number of acquisition steps on a per included angle basis for the second range 2720 relative to the other ranges. Thus, a relatively larger number of acquisition steps are made during the range of interest, which corresponds to the second range 2720 shown in FIG. 27, than for other ranges. Similar to the example discussed in connection with FIG. 26, the depicted dwell time 2707 is about the same for the first range 2710 and the third range 2730. The dwell time 2708 for the second range 2720 is longer than the dwell time 2707. Thus, more time is spent acquiring information for a given step during the range of interest than other ranges. Alternatively, in various embodiments, the dwell time may be held constant while the sweep step varies as shown in FIG. 27. FIG. 27 provides an example of non-uniform angular sampling utilized in conjunction with a non-uniform or non-constant time per view.

Figure 28:
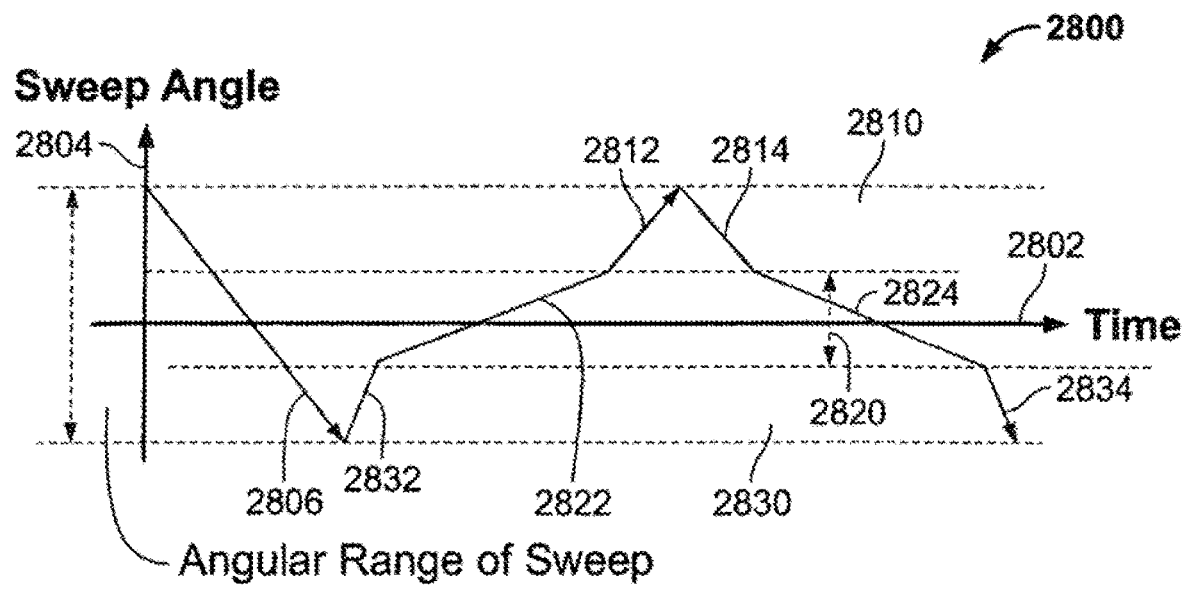
FIG. 28 illustrates another example of varying sweep rate in accordance with various embodiments.

FIG. 28 illustrates another example of varying sweep rate in accordance with various embodiments, wherein a continuous scanning is used. This is in contrast to FIGS. 26-27, where the detector remains motionless for some periods of time (as denoted by the horizontal sections in the graph), with the data acquisition performed mainly while the detector is motionless in FIGS. 26-27. In FIG. 28, a curve 2800 depicts rotation of a detector along a horizontal axis 2802 corresponding to time and a vertical axis 2804 corresponding to sweep angle, or rotation or pivoting of the detector. As seen in FIG. 28, the detector is rotated through a first range 2810, a second range 2820, and a third range 2830. The second range 2820 corresponds to a range of interest or range of focus, while the first range 2810 and the third range 2830 correspond to ranges of lesser interest. As seen in FIG. 28, the slope during the range of interest (corresponding to second range 2820) is less than the slope during the other ranges, depicting slower rotation and increased information collection during the range of interest. In FIG. 28, while there are changes of slope depicted at transition points between ranges, the rotation of the detector is performed substantially continuously.

FIG. 28 also includes a first portion 2806 at a relatively high slope or rate of rotation. The first portion 2806 in the illustrated embodiment corresponds to the performance of a scout scan. During the depicted scout scan, the sweep rate or rotational speed is substantially the same for all ranges, and no sweep focusing (e.g., slowing down a sweep rate during a range of interest) is performed. However, subsequent rotation of the detector is controlled to provide focusing during the second range 2820. As seen in FIG. 28, the detector is rotated at a relatively high rate during the portions 2812, 2814 of the first range 2810, and during the portions 2832, 2834 of the third range. However, the detector is rotated at a relatively low rate during the portions 2822, 2824 of the second range 2820. The portions 2822, 2824 may be understood as providing a focused sweep. As shown in FIG. 28, more time is spent acquiring information for a given angular range during the range of interest than other ranges. The variation in slopes between the ranges may be selected to provide sufficient information acquisition during the range of interest to provide clinically useful imaging results, while providing, for example, sufficient information during other ranges to provide adequate artifact correction and/or registration with images obtained using other modalities. As shown in FIG. 28, in various embodiments, plural rotations through the ranges may be performed during imaging information acquisition. Information collected at corresponding angular positions (e.g., a specified range of angular positions) for different rotations may be binned together for reconstruction. Since data is acquired while the detector is in motion, the data may be stored in a way that allows association of each acquired photon with the direction from which it most likely arrived. Several methods may be used. As one example, in some embodiments, a list mode, in which parameters of each detected photon are saved together with data indicative of the orientation of the detector at the time of the photon detection, may be employed. For instance, readings of angular encoders may be saved together with the photon data, or interspersed within the data set. As yet another example, a timed list mode may be employed in various embodiments. In a timed list mode, each photon may be associated with a time-stamp, such that the time of detection may be associated to each detected photon. Similarly, the angular orientation of the detectors may be associated with the time, such that the orientation of the detector may be deciphered for the time of each photon detection. It may be noted that gantry and/or bed motion may be continuous, and the positions of the gantry and/or bed may be similarly associated with the detected photons. As yet one more example, a re-binning method may be employed. In the re-binning method, the scanning range is divided into small sections or "views." For instance, a first view may be defined as an angular orientation α in the range A0≤α≤A1; a second view may be defined when α is in the range A1≤α≤A2; and so on. It may be noted that photons detected on a return swing of the detector may be re-binned into the same views as photons detected in the forward swing (in contrast to a list mode that is generally a chronological logging of detected events). Re-binning may be done in real time, thus reducing data file size and storage space. Alternatively or additionally, re-binning may be done from a list-mode file. In some embodiments, re-binning may be performed from the list-mode, off-line and using different set of views. Further, reconstruction may be performed using re-binned views. For example, OSEM (Ordered Sub-Set Expectation Maximization) algorithms may be employed. Additional discussion of the use of event-oriented reconstruction algorithms is provided in U.S. Pat. No. 7,671,331, "Apparatus and Methods for Processing Imaging Data from Mulitple Detectors," issued Mar. 2, 2010, the content of which is incorporated by reference herein in its entirety.

Figure 29:
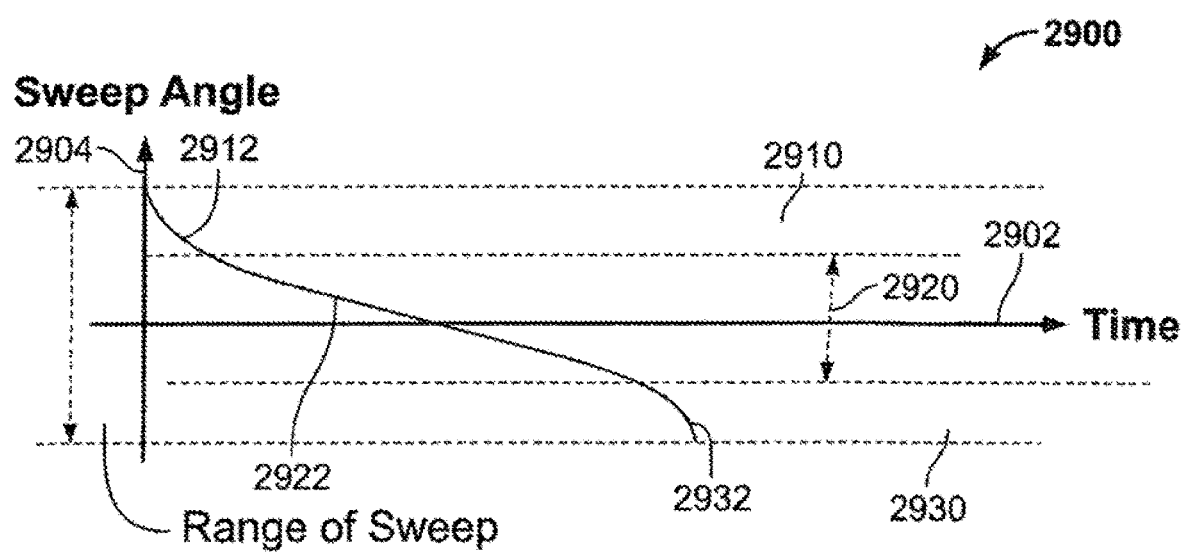
FIG. 29 illustrates another example of varying sweep rate in accordance with various embodiments.

FIG. 29 illustrates another example of varying sweep rate in accordance with various embodiments. In FIG. 29, a curve 2900 depicts rotation of a detector along a horizontal axis 2902 corresponding to time and a vertical axis 2904 corresponding to sweep angle, or rotation or pivoting of the detector. As seen in FIG. 29, the detector is rotated through a first range 2910, a second range 2920, and a third range 2930. The second range 2920 corresponds to a range of interest or range of focus, while the first range 2910 and the third range 2930 correspond to ranges of lesser interest. As seen in FIG. 29, the slope during the range of interest (corresponding to second range 2920) is generally less than the slope during the other ranges, depicting slower rotation and increased information collection during the range of interest. In FIG. 29, the changes of slope are depicted as changing gradually and generally continuously along transition portions between ranges. The lower slope of the range of the second range 2920 (corresponding to a range of interest) extends beyond the second range 2920 and into other ranges. The extension of the lower slope and continuous change of slope depicted in FIG. 29 provides a smooth transition between rotational speeds and a safety margin of relatively high amounts of information acquisition around the range of interest.

As seen in FIG. 29, the detector is rotated at a relatively high rate during the portion 2912 of the first range 2910 and during the portion 2932 of the third range 2930. However, the detector is rotated at a relatively low rate during the portion 2922 of the second range 2920. The portion 2922 may be understood as providing a focused sweep. As shown in FIG. 29, more time is spent acquiring information for a given angular range during the range of interest than other ranges.

It may be noted that, in various embodiments, continuous acquisition may be performed in conjunction with CT scanning and/or scout emission data. Also, data acquired during continuous acquisition may be re-binned into views, with each view containing data that was acquired in a limited, corresponding angular range. Further, data acquired during continuous acquisition may be saved with a list mode (including event data and detector orientation data), and reconstructed using an event-oriented reconstruction algorithm.

Figure 30:
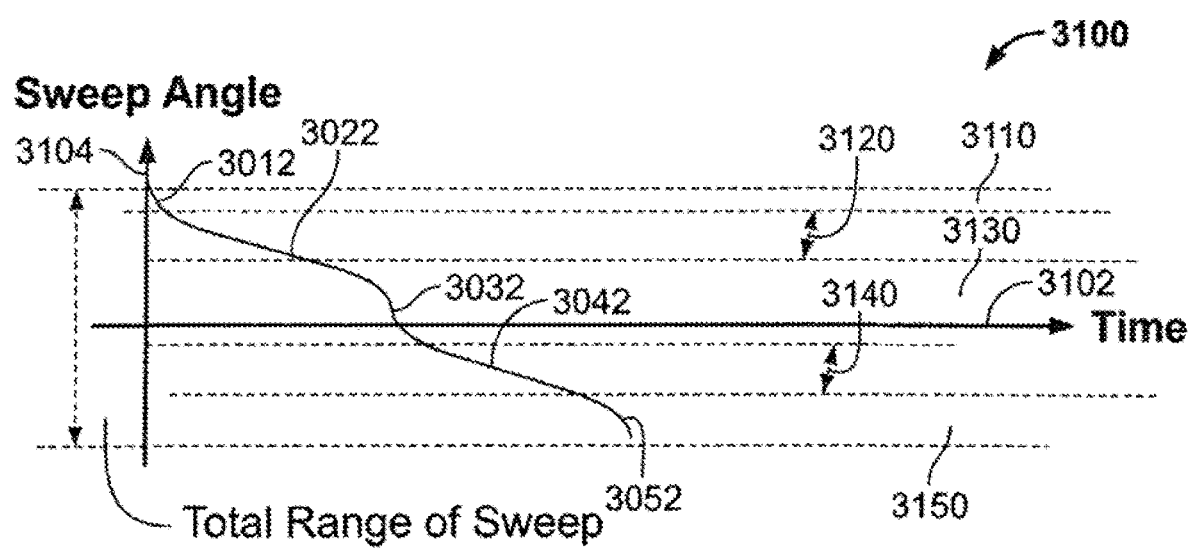
FIG. 30 illustrates another example of varying sweep rate in accordance with various embodiments.

FIG. 30 illustrates another example of varying sweep rate in accordance with various embodiments. The embodiment depicted in FIG. 30 is similar to FIG. 29 in certain general respects; however, in FIG. 30, two ranges of interest are depicted. The two ranges of interest may correspond, for example, to the bones of two legs (see, e.g., FIG. 25 and related discussion). In FIG. 30, a curve 3000 depicts rotation of a detector along a horizontal axis 3002 corresponding to time and a vertical axis 3004 corresponding to sweep angle, or rotation or pivoting of the detector. As seen in FIG. 30, the detector is rotated through a first range 3010, a second range 3020, a third range 3030, a fourth range 3040, and a fifth range 3050. The second range 3020 and the fourth range 3030 correspond to ranges of interest or ranges of focus, while the first range 3010, the third range 3030, and the fifth range 3050 correspond to ranges of lesser interest. As seen in FIG. 30, the slope during the ranges of interest (corresponding to second range 3020 and the fourth range 3040) is generally less than the slope during the other ranges, depicting slower rotation and increased information collection during the ranges of interest. As seen in FIG. 30, the detector is rotated at a relatively high rate during the portion 3012 of the first range 3010, during the portion 3032 of the third range 3030, and during the portion 3052 of the fifth range 3050. However, the detector is rotated at a relatively low rate during the portion 3022 of the second range 3020 and the portion 3042 of the fourth range 3040. The portion 3022 and the portion 3042 may be understood as providing a focused sweep. As shown in FIG. 30, more time is spent acquiring information for a given angular range during the ranges of interest than other ranges. Two distinct organs of interest that may correspond to the ranges of interest may be (but not limited to) limbs, as one example, or kidneys, as another example.

Figure 31:
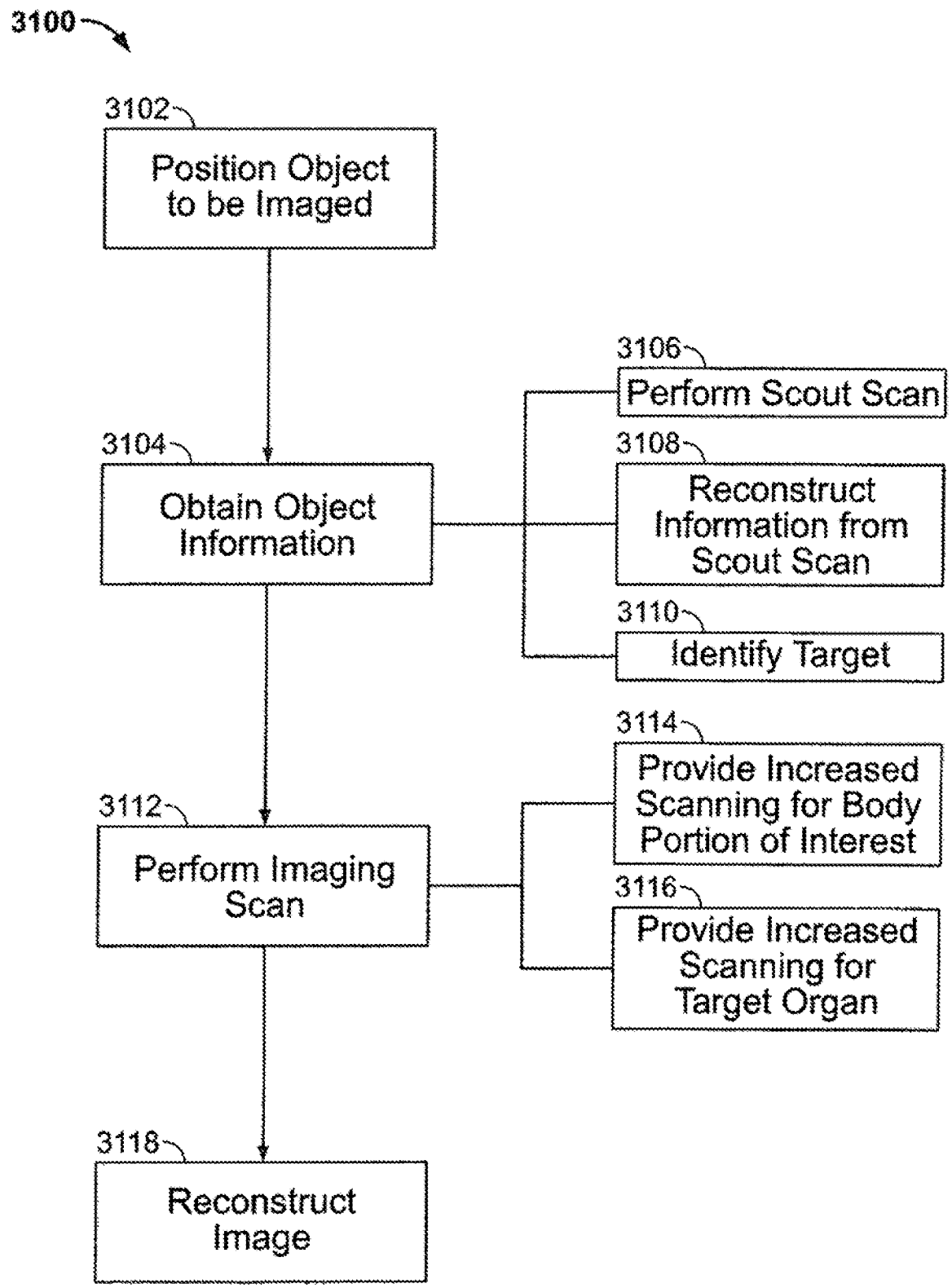
FIG. 31 is a flowchart of a method for imaging an object in accordance with various embodiments.

FIG. 31 provides a flowchart of a method 3100 for imaging an object (e.g., a portion of a human or animal patient) in accordance with various embodiments. The method 3100, for example, may employ or be performed by structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 3100 may be able to be used as one or more algorithms to direct hardware to perform one or more operations described herein.

At 3102, the object to be imaged is positioned. The object, for example, may be a human patient. The patient may be placed on a bed that may be advanced through a gantry (e.g., a gantry including plural SPECT detectors or detector units) for imaging of the patient. The bed may also be advanced to position the patient for scanning with a different modality, such as CT. It may be noted that the position of the patient may be changed during various portions of image acquisition. For example, the patient may be positioned differently during a scout scan and a subsequent imaging scan, and/or the patient may be positioned differently (e.g., advanced through the bore) to allow scanning of different portions along the length of the patient.

At 3104, object information corresponding to the object (e.g., patient) to be imaged is obtained. The object information in various embodiments includes information describing, depicting, or otherwise corresponding to a body shape and internal structure of a patient being imaged that is sufficient to allow identification of one or more volumes of interest. The object information may be obtained by an imaging unit or other device and provided to a processing unit that in turn identifies the location of the one or more volumes of interest. It may be noted that while various techniques may be employed to obtain the object information, an example using a scout scan will be discussed below in connection with steps 3106, 3108, and 3110.

At 3106, a scout scan or acquisition is performed. The scout scan may be performed, for example as a CT scan. In other embodiments, the scout scan or acquisition may be performed by acquiring emission information. The scout scan is generally performed at a relatively high speed and at a low resolution. In some embodiments, information from the scout scan may not provide sufficient resolution or quality for conventional and/or diagnostic imaging.

At 3108, information obtained during the scout scan at 3106 is reconstructed. The reconstruction may result in a generally poor quality image, but have enough information to identify one or more volumes of interest for a subsequent imaging scan. The volume of interest, for example, may include one or more target organs.

At 3110, a target for focused scanning is identified. As used herein, a target for focused scanning may be understood as a portion of an object being imaged for which a relatively large amount of scanning information is desired relative to at least one other portion of the object. For example, for a scan to be used in conjunction with a diagnosis or an analysis related to the liver, the liver may be identified as a target for focused scanning, while other organs (e.g., the lungs, kidneys, intestines, or the like) may not be identified as targets for focused scanning. Focused scanning may be subsequently performed spending a greater proportion of time collecting information corresponding to the liver than to other organs to provide a higher amount and/or quality of image information for the liver than other organs, improving image quality while reducing time spent on portions of the body for which detailed imaging information may not be required, thereby providing efficient scanning times. In various embodiments, a target organ (or organs) may be identified, and appropriate scan parameters (e.g., positioning of detectors, ranges of rotation or pivoting of detectors, sweep rate during different portions of the rotation or pivoting of the detectors) may be determined by one or more processing units and/or one or more controllers. It may be noted that an identified volume for focused scanning may also include a safety margin around the target organ or organs. In some embodiments, using a 3D image generated at 3108, a target organ may be identified automatically by a processing unit using automatic image processing software, for example based on a known general shape and density of the target organ, and/or the general shape and density of non-target organs near the target. Additionally or alternatively, manual inputs (e.g., by an operator identifying locations on the boundaries of the VOI) may be employed in semi-automatic or manual approaches. In some cases, a patient atlas (e.g., a typical patient atlas corresponding to a standard human patient) may be employed in automatic, semi-automatic or manual determination of the VOL In various embodiments, a patient atlas may be tailored or otherwise correspond to a group or sub-group of patient types (e.g., patient atlases may be sub-diveded by weight, height, and/or gender, among others.)

At 3112, an imaging scan is performed. In some embodiments, the imaging scan may be performed using plural SPECT detector units disposed around a bore of a gantry, with the plural detector units positioned proximate to surfaces of the object to be imaged (e.g., a portion of a patient). In some embodiments the detector units may be translated vertically (e.g., with respect to a horizontal plane defined by a patient bed), while the detector units may be translated radially in other embodiments to position the detector units proximate the object to be scanned. The rotation of the detector units in various embodiments is controlled to increase scanning time (and amount of information acquired) when volumes of interest (e.g., target organs) are within view of the detector units, and to reduce scanning time when volumes of interest are not within view of the detector units. Thus, one or more detector units may be rotated at a variable sweep rate to provide focused scanning. Accordingly, in various embodiments, performing the imaging scan may include rotating at least one detector unit at a sweep rate from a first position to a second position defining a range of view of the object to be imaged to acquire the scanning information, and varying the sweep rate during the rotation from the first position to the second position to obtain a larger amount of scanning information for at least one portion of the object of interest than for at least one portion of lesser interest. It may be noted that the rotation may be performed continuously or in discrete steps. In various embodiments, the focused scanning may be provided based on a length along the patient and/or a location within a volume of the patient being scanned.

For example, at 3114, an increased time (slower sweep and increased information acquisition) is provided for a body portion of interest along the length of a patient undergoing a whole body scan. In one example scenario, a whole body scan may be performed in which a physician desired improved imaging for the torso of the patient relative to other portions. Thus, for example, a slower sweep rate may be provided while scanning the torso relative to other portions of the body.

As another example, at 3116, an increased time (slower sweep and increased information acquisition) is provided for a target organ within a volume being imaged. For example, a bone of a leg may be the target organ in an example scenario. In such a scenario, a slower sweep rate may be provided for detector units when the bone is in view of the detector units than when the bone is not. It may be noted that detector units may move independently in and out as the patient is moved, to position the detectors near the patient body (e.g., using body contouring methods).

At 3118, an image is reconstructed. The image may be reconstructed using information obtained during the imaging scan. Information from other scans (e.g., a scout scan or other modality scan) may be used in some embodiments. Information at a higher resolution and/or lower noise level for a volume of interest (e.g., target organ) may be used while information at a lower resolution and/or higher noise lever for other portions of an object may be used. The lower resolution and/or higher noise level information may be used for example, in connection with artifact removal and/or registration to other images, or as another example, to provide an image including tissue surrounding a volume of interest. It may be noted that imaging techniques such as binning or gating, among others, may be employed in various embodiments.

As indicated herein (see, e.g., FIGS. 6-14 and related discussion), collimators may be employed in connection with the detector units. In various embodiments, multi-hole collimators (e.g., collimators including more than one bore per pixel of a detector) may be employed. For example, in some embodiments, collimators providing four bores per pixel may be utilized. The use of plural bores per pixel may permit the reduction of collimator height while maintaining similar resolution and sensitivity (e.g., when compared to a taller collimator having one bore per pixel). Reduction in collimator height may be used to reduce the diameter of a detector unit, thereby allowing additional detectors (and additional views and information to be collected) to be placed around an object to be scanned. Also, reduction in collimator height may be used to reduce the minimal scannable diameter by a group of detector units disposed around a volume of interest, such as the brain, without creating overly large gaps between the faces of one or more collimators and the object being scanned, thus improving system resolution. Further, use of, for example, four bores per collimator may be utilized to improve the resolution for the same collimator to body distance relative to single bore collimators. Collimators using multiple bores per pixel may be used, for example, in connection with other embodiments disclosed herein.

Examples of collimators including multiple bores per pixel are provided in U.S. Patent Applicant Publication No. 2013/0168567 (the '567 Application), entitled "Collimator For a Pixelated Detector," filed Dec. 28, 2011, the entire subject matter of which is incorporated herein by reference. The '567 Application discloses, among other things, a collimator for collimating gamma photons that may be used in medical imaging (e.g., nuclear medicine). The collimator has holes through a height of the collimator, with the holes arranged in groups of clusters. The collimator may be used with a detector having an array of pixels, with each group of holes associated with a corresponding pixel, thereby providing multiple collimator holes per pixel.

Figure 32:
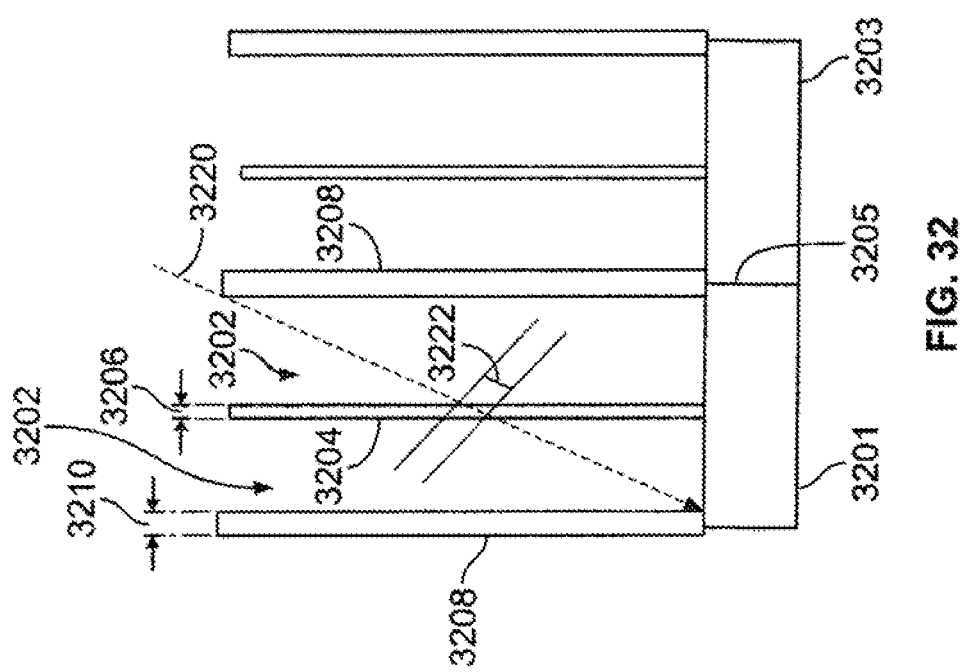
FIG. 32 illustrates a side cross-section of a collimator in accordance with various embodiments.

In various embodiments, as shown in FIG. 32, a group of holes 3202 (or bores) of a pixel 3201 may include walls 3204 or septa of a first width 3206 separating the holes (or bores) of the particular group, and walls 3208 or septa of a second width 3210 separating the holes (or bores) of the particular group from a neighboring group of a neighboring pixel 3203 separated from the pixel 3201 at a boundary 3205. The second width 3210 may be greater than the first width 3206. For example, a thinner width for interior or central septa may be employed, as large angles of entry into a bore may already be blocked by exterior or main septa (which have the greater thickness of the second width 3210). Further, as angles of entry permitted by the exterior or main septa are relatively large, the effective thickness of the interior or central septa is relatively large. As shown in FIG. 32, at steeper angles, a line of entry 3220 has a greater length 3222 of passage through the interior or central septa than for shallower angles.

Figure 33:
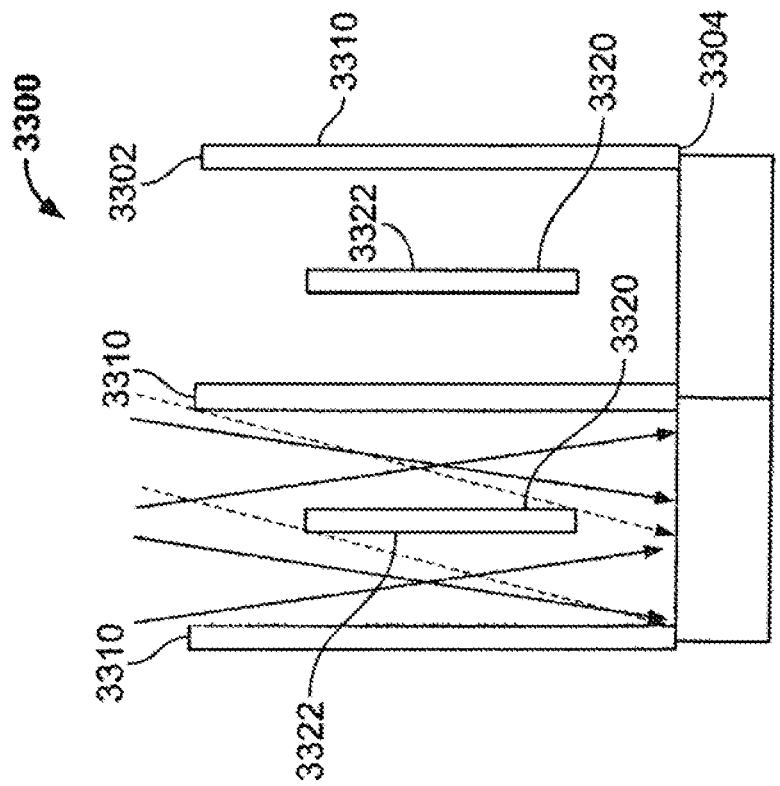
FIG. 33 illustrates a side cross-section of a collimator in accordance with various embodiments.

Alternatively or additionally, the interior or central septa may be recessed from a top and/or bottom of the collimator as shown in FIG. 33. FIG. 33 depicts a collimator 3300 including a top 3302 and a bottom 3304. The exterior walls 3310 extend from the top 3302 to the bottom 3304, while the interior walls 3320 are recessed from the top 3302 and recessed from the bottom 3304. The central portion 3322 of the interior walls 3322 may act to block highly slanted beams that pass the exterior walls 3310.

As discussed herein (see, e.g., FIGS. 5-14 and related discussion), various collimator configurations may be employed to provide varying ratios of sensitivity or resolution between centers and sides of a detector unit and collimator. It may be noted that such configurations may be employed in collimators having multiple bores per pixel.

Figure 35:
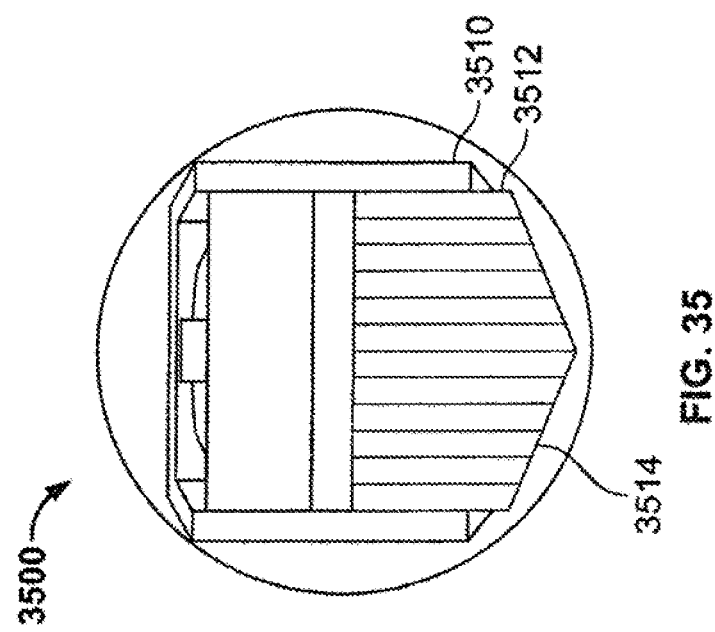
FIG. 35 illustrates a side view of a collimator in accordance with various embodiments.
Figure 34:
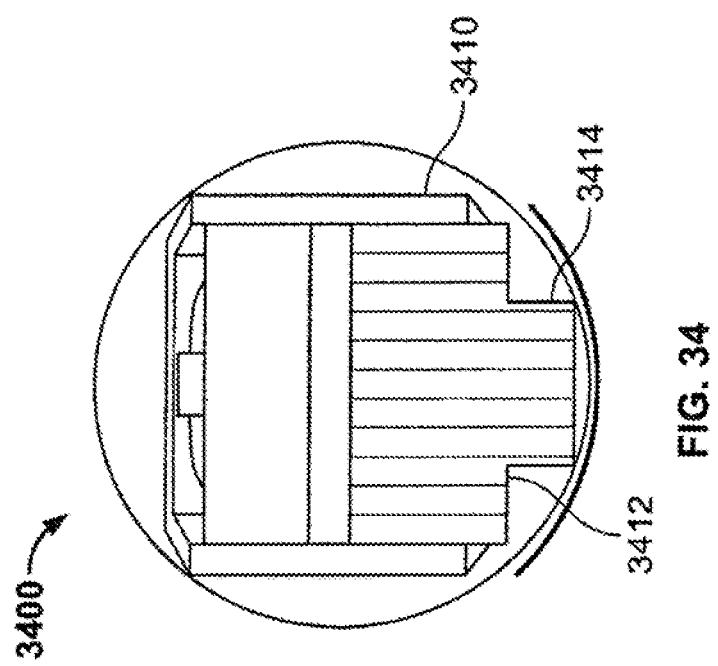
FIG. 34 illustrates a side view of a collimator in accordance with various embodiments.

FIG. 34 illustrates a detector unit 3400 including a collimator 3410 having a first portion 3412 and a face 3414. As seen in FIG. 34, the face 3414 is generally rectangular shaped and provides additional length to collimator tubes or bores toward a central portion of the collimator 3410. Accordingly, as a result of the longer bore lengths in the central portion, a higher resolution imaging portion or area is defined when compared to the shorter lengths of bores in the sections of the first portion 3412 disposed laterally outwardly from the face 3414. As another example, FIG. 35 illustrates a detector unit 3500 including a collimator 3510 including a first portion 3512 and a face 3514. As seen in FIG. 35, the face 3514 has generally triangular profile providing a maximum bore length at the center of the collimator 3510. Other shapes or profiles for the face 3514 may be employed in various embodiments.

Figure 36:
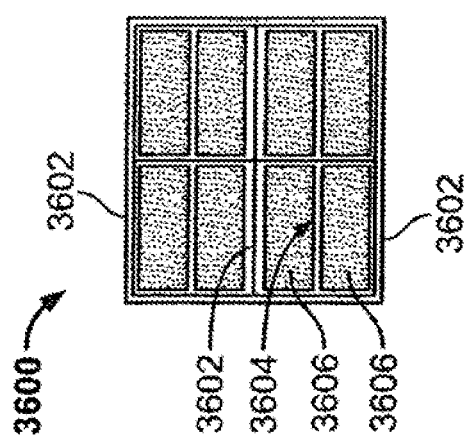
FIG. 36 illustrates a top view of a collimator in accordance with various embodiments.

It may be noted that the bores of a group of bores for a given pixel may be isotropic in various embodiments. In alternate embodiments, the bores of a given pixel may be anisotropic or differently sized. FIG. 36 provides a top view of a collimator 3600 having anisotropic bores for one or more pixels. As seen in FIG. 36, the collimator 3600 includes main or external septa 3602 and internal septa 3604 defining anisotropic bores 3606 that are rectangular (but not square) in cross-section. The arrangement shown in FIG. 36 is provided by way of example and not limitation, as other numbers of bores per pixel and/or shapes and/or arrangements may be employed in various embodiments.

Figure 37:
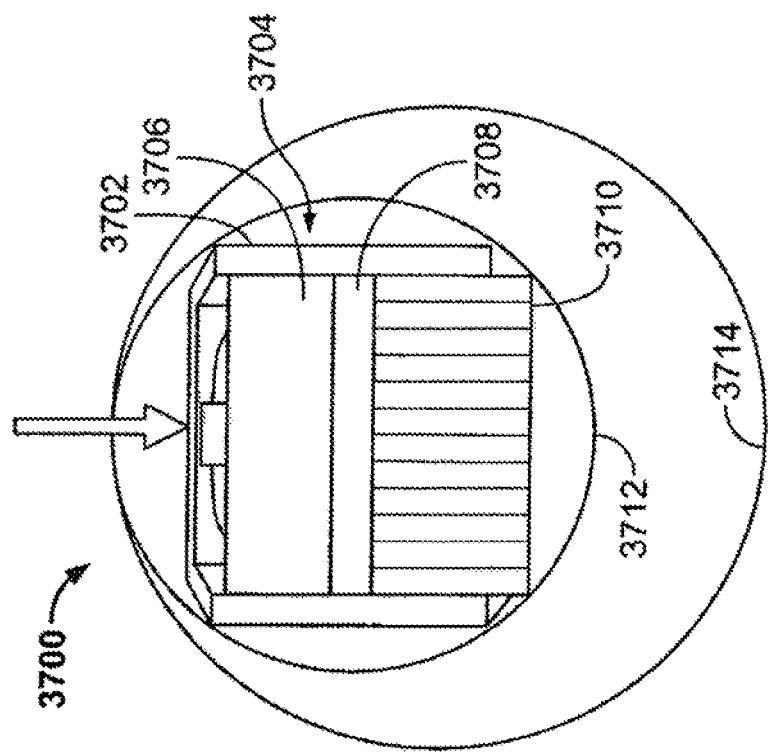
FIG. 37 illustrates a side view of a collimator in accordance with various embodiments.

As discussed herein, use of multiple collimator bores per pixel may be employed to reduce the overall size of detector unit. FIG. 37 illustrates a detector unit 3700 including shielding 3702, a detector module 3704 including electronics 3706 coupled to a CZT pixelated detector 3708, and a 4-hole collimator 3710. Use of the 4-hole collimator 3710 provides an envelope 3712 that is smaller than an envelope 3714 required for a longer collimator using only one bore per pixel. The shielding 3702 may also be configured to act as a holder, further reducing the number of parts required and/or the size of the detector unit 3700. In the illustrated embodiment, the shielding 3702 may be comprised of, for example, a tungsten or lead alloy. As another example, the shielding 3702 may be comprised of tungsten powder in a matrix of epoxy. The epoxy may be a structural material with high absorption coefficient. Such shielding may provide further reduction in size or miniaturization.

The reduction in size of the detector unit 3700 may provide a number of benefits. For example, smaller detector heads allow for denser packing or positioning of detectors around an object to be imaged, improving camera sensitivity. Use of smaller detector heads may also reduce the colliding of detector heads when imaging smaller objects and allowing use of more detectors and reduced gaps between detectors for smaller objects to be scanned, as well as allowing detectors to be more closely positioned to smaller objects.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

What is claimed is:

1. An imaging system comprising:
a gantry;

at least five detector units mounted to the gantry, each of the detector units comprising a plurality of pixels;

a corresponding collimator for each of the at least five detector units, each collimator configured to be interposed between the detector unit and an object to be imaged, the collimator having septa defining plural bores for each pixel of at least some of the plurality of pixels of the detector unit, the septa comprising interior septa aligned over corresponding interior portions of the at least some of the pixels and exterior septa aligned over borders of the at least some of the pixels;

at least one processing unit configured to obtain object information corresponding to the object to be imaged, the processing unit comprising a tangible and non-transitory computer readable storage medium having instructions configured to direct the processor to perform operations; and a controller configured to control an independent rotational movement of each the at least five detector units used to acquire scanning information by detecting emissions from the object, wherein the controller rotates each of the detector units at a corresponding sweep rate.

2. The imaging system of claim 1, wherein the exterior septa are differently sized from the interior septa.

3. The imaging system of claim 2, wherein the exterior septa extend along a length from a top to a bottom of the collimator, and wherein the interior septa do not extend to at least one of the top or the bottom of the collimator.

4. The imaging system of claim 1, wherein the septa comprise interlocking sheets of gamma absorbing material.

5. The imaging system of claim 1, wherein the collimator includes four bores for each pixel of the at least some of the plurality of pixels.

6. The imaging system of claim 1, wherein the collimator defines a face having longer bore lengths toward a central portion of the collimator.

7. The imaging system of claim 6, wherein the collimator comprises a central rectangular portion defining a longer bore length than an adjacent rectangular portion disposed laterally outwardly from the central rectangular portion.

8. The imaging system of claim 6, wherein the face has a generally triangular profile.

9. The imaging system of claim 6, wherein the face has a curved profile.

10. The imaging system of claim 9, wherein the curved profile corresponds to a section of a face of a cylinder centered at a center of rotation of the detector unit.

11. The imaging system of claim 1, wherein the collimator has variable bore lengths, and wherein the collimator comprises interlocking sheets having complementary cuts configured for interlocking the sheets together.

12. The imaging system of claim 1, wherein at least some of the bores have an anisotropic cross-section.

13. The imaging system of claim 12, wherein the at least some of the bores have a non-square rectangular cross-section.

14. An imaging system comprising:

a gantry;

at least five detector units mounted to the gantry, each of the detector units comprising a plurality of pixels;

a corresponding collimator for each of the at least five detector units, each collimator configured to be interposed between the detector unit and an object to be imaged, the collimator having septa defining bores, wherein the collimator defines a face having longer bore lengths toward a central portion of the collimator;

at least one processing unit configured to obtain object information corresponding to the object to be imaged; and a controller configured to control an independent rotational movement of each the at least five detector units used to acquire scanning information by detecting emissions from the object, wherein the controller rotates each of the detector units at a corresponding sweep rate.

15. The imaging system of claim 14, wherein the face has a curved profile.

16. The imaging system of claim 15, wherein the curved profile corresponds to a section of a face of a cylinder centered at a center of rotation of the detector unit.

17. The imaging system of claim 2, wherein the exterior septa are thicker than the interior septa.

* * * * *